(12) United States Patent
Kumagai et al.

(10) Patent No.: US 12,303,590 B2
(45) Date of Patent: *May 20, 2025

(54) METHOD OF TREATING OSTEOARTHRITIS

(71) Applicant: ORTHOTROPHIX, INC., Oakland, CA (US)

(72) Inventors: Yoshinari Kumagai, Foster City, CA (US); Dawn McGuire, Orinda, CA (US); Meghan Miller, Antioch, CA (US); David Rosen, New Braunfels, TX (US)

(73) Assignee: OrthoTrophix, Inc., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/517,533

(22) Filed: Nov. 2, 2021

(65) Prior Publication Data

US 2022/0047501 A1 Feb. 17, 2022

Related U.S. Application Data

(63) Continuation of application No. 16/586,516, filed on Sep. 27, 2019, now abandoned.

(60) Provisional application No. 62/838,712, filed on Apr. 25, 2019, provisional application No. 62/811,366, filed on Feb. 27, 2019, provisional application No. 62/787,881, filed on Jan. 3, 2019, provisional application No. 62/775,056, filed on Dec. 4, 2018.

(51) Int. Cl.
| | |
|---|---|
| *A61K 38/17* | (2006.01) |
| *A61B 5/00* | (2006.01) |
| *A61B 5/055* | (2006.01) |
| *A61B 5/103* | (2006.01) |
| *A61K 9/00* | (2006.01) |
| *A61K 38/16* | (2006.01) |
| *A61P 19/02* | (2006.01) |
| *C07K 14/47* | (2006.01) |

(52) U.S. Cl.
CPC ............ *A61K 9/0019* (2013.01); *A61B 5/055* (2013.01); *A61B 5/103* (2013.01); *A61B 5/4504* (2013.01); *A61B 5/4514* (2013.01); *A61B 5/4528* (2013.01); *A61B 5/4585* (2013.01); *A61K 38/16* (2013.01); *A61K 38/1709* (2013.01); *A61P 19/02* (2018.01); *C07K 14/47* (2013.01); *A61B 5/4824* (2013.01)

(58) Field of Classification Search
CPC .............................. A61K 38/16; A61P 9/0019
See application file for complete search history.

(56) References Cited

U.S. PATENT DOCUMENTS

| | | | |
|---|---|---|---|
| 7,638,486 B2 | 12/2009 | Lazarov et al. | |
| 7,888,462 B2 | 2/2011 | Middleton-Hardie | |
| 8,426,558 B2 * | 4/2013 | Middleton-Hardie | A61P 29/00 530/324 |
| 8,426,588 B2 | 4/2013 | Makino | |
| 11,278,413 B1 | 3/2022 | Lang | |
| 2002/0147392 A1 | 10/2002 | Steines et al. | |
| 2008/0096798 A1 | 4/2008 | Lazarov et al. | |
| 2009/0062201 A1 | 3/2009 | Kumagai et al. | |
| 2011/0105401 A1 | 5/2011 | Middleton-Hardie et al. | |
| 2011/0202032 A1 | 8/2011 | Shih et al. | |
| 2011/0266265 A1 | 11/2011 | Lang | |
| 2016/0296692 A1 | 10/2016 | Agris | |
| 2019/0388503 A1 | 12/2019 | Kumagai et al. | |
| 2020/0002393 A1 | 1/2020 | Kumagai et al. | |
| 2020/0009220 A1 | 1/2020 | Kumagai | |
| 2020/0170939 A1 | 6/2020 | Kumagai et al. | |
| 2022/0133484 A1 | 5/2022 | Lang | |

FOREIGN PATENT DOCUMENTS

| | | | | |
|---|---|---|---|---|
| CN | 1559634 A | 1/2005 | | |
| CN | 103505628 A | 1/2014 | | |
| CN | 107998488 A | 5/2018 | | |
| CN | 108773893 A | 11/2018 | | |
| KR | 20180015810 A | 2/2018 | | |
| WO | WO 2008/091632 | 7/2008 | | |
| WO | WO-2010018407 A1 * | 2/2010 | ............ | A61B 6/505 |

OTHER PUBLICATIONS

Sayre et al., PLOS ONE, May 4, 2017, 12(5):e0176833.*
Hayashi et al., Annals of Physical and Rehabilitation Medicine, 2016, vol. 59:161-169.*
"Cartilage Protection and Formation Have Failed to Move DMOAD Development Forward" OrthoTrophix, 1 page (2021).
"Guidance for Industry, Clinical Development Programs for Drugs, Devices, and Biological Products Intended for the Treatment of Osteoarthritis (OA)" U.S. Department of Health and Human Services, Food and Drug Administration, Center for Drug Evaluation and Research (CDER), Center for Biologics Evaluation and Research (CBER), Center for Device and Radiological Health (CDRH) (Jul. 1999) 12 pages.
Hochberg, et al., "Efficacy and Safety of Intra-Articular Sprifermin in Symptomatic Radiographic Knee Osteoarthritis: Results of the 2-Year Primary Analysis from a 5-Year Randomised, Placebo-Controlled, Phase II Study" 2017 ACR/ARHP Annual Meeting (Oct. 19, 2017) Abstract No. 1L, 4 pages.

(Continued)

*Primary Examiner* — Xiaozhen Xie
(74) *Attorney, Agent, or Firm* — Andrew R. Guzman; Bozicevic, Field & Francis LLP

(57) ABSTRACT

A method of treating osteoarthritis by modifying the shape change of bone(s) underlying articular cartilage, comprising evaluating the bone shape of the patient's joint, injecting the patient with a peptide of SEQ ID No. 1 or applying other therapeutic interventions that can reduce the shape change of the bone(s) underlying articular cartilage, and thereafter evaluating the bone shape of the patient's joint is disclosed.

4 Claims, 15 Drawing Sheets

Specification includes a Sequence Listing.

(56) References Cited

OTHER PUBLICATIONS

Hochberg, et al., "Efficacy and Safety of Intra-articular Sprifermin in Symptomatic Radiographic Knee Osteoarthritis: Pre-specified Analysis of 3-Year Data from a 5-Year Randomized, Placebo-Cotnrolled, Phase II Study" Osteoarthritis and Cartilage (2018) 26:S26-S27) Abstract No. 32.
"Osteoarthritis: Structural Endpoints for the Developments of Drugs, Devices, and Biological Products for Treatment, Guidance for Industry" U.S. Department of Health and Human Services, Food and Drug Administration, Center for Drug Evaluation and Research (CDER), Center for Biologics Evaluation and Research (CBER), Center for Device and Radiological Health (CDRH) (Aug. 2018) 6 pages.
"Patella Cartilage Thickness Change from Baseline" and "Tibiofemoral Cartilage Thickness Change from Baseline" OrthoTrophix (2021).
McGuire et al. "Significant, Sustained Improvement in Knee Function after Intra-Articular TPX-100: A Double-Blind, Randomized, Multi-Center, Placebo-Controlled Phase 2 Trail." 2017 ACR Poster.
McGuire et al. "TPX-100 Leads to Marked, Sustained improvements in Subjects with Knee Osteoarthritis: Pre-Clinical Rationale and Results of a Controlled Clinical Trial" 2018 OARSI Poster.
McGuire et al. "Improved Knee Physical Function Correlates Significant with TF Cartilage Thickness Increase after IA TPX-100: Results of a Post Hoc Analysis" 2019 EULAR Abstract.
McGuire et al. "Improved Knee Physical Function Correlates Significantly with TF Cartilage Thickness after IA TPX-100: Results of a Post Hoc Analysis" 2019 EULAR Poster.
McGuire et al. "Study TPX-100-5: Intra-articular TPX-100 Significantly Delays Pathological Bone Shape Change at 6 and 12 Months in Moderate and Sever Tibiofemoral OA" 2019 ACR Bone Shape Poster.
McGuire et al. "Stabilization of Patellar Bone-Shape Correlates Significantly with Reduced Knee Pain Frequency After IA TPX-100 in Subjects with Bilateral Patellofemoral OA" 2019 ACR Pain Abstract.
McGuire et al. "Stabilization of Patellar Bone-Shape Correlates Significantly with Reduced Knee Pain Frequency after IA TPX-100 in Subjects with Bilateral Patellofemoral OA" 2019 ACR Pain Poster.
McGuire et al. "Study TPX-100-5: Intra-Articular TPX-100 Significantly Delays Pathological Bone Shape Change and Stabilizes Cartilage in Moderate to Sever Bilateral Knee OA" 2021 ART Paper.
Karsdal et al., "Disease-modifying treatments for osteoarthritis (DMOADs) of the knee and hip: lessons learned from failures and opportunities for the future" Osteoarthritis and Cartilage (2016) 24(12)2013-2021.
McGuire et al., "TPX-100 Leads to the Marked, Sustained Improvements in Subjects with Kneww Osteoarthritis: Pre-Clinical Rationale and Results of a Controlled Clinical Trial" Osteoarthritis and Cartilage (2018) 26(1):S243.
Walsh et al., "Treating People With Joint Pain" International Association for the Study of Pain (2016) pp. 1-4.
Hu et al., "Joint level-set shape modeling and appearance modeling for brain structure segmentation" NeuroImage, 36:672-683 (2007).

McGuire, "TPX-100 Leads to Marked, Sustained improvements in Subjects with Knee Osteoarthritis: Pre-Clinical Rationale and Results of a Controlled Clinical Trial" Abstracts for Osteoarthritis and Cartilage, 26:#463 (2018).
Neogi et al., "MRI-based three dimensional bone shape of the knee predicts onset of knee osteoarthritis: Data from the Osteoarthritis Initiative" Arthritis Rheum, 65(8):2048-2058 (2013).
Orthotrophix, "A Randomized, Double-blind, Placebo-controlled, Multi-dose Phase 2 Study Evaluating the Safety and Efficacy of Intra-articular Injections of TPX-100 in Subjects with Mild to Moderate Patello-Femoral Osteoarthritis Involving Both Knees," Dialog, NCT01925261 (Aug. 15, 2013).
Perry et al., "Measurement of synovial tissue volume in knee osteoarthritis using a semiautomated MRI-based quantitative approach" Magn Reason Med, 81:3056-3064 (2019).
AC-100 from https://www.drubank.ca.drugs/DB05671, pp. 1-3. Accessed Apr. 4, 2020 (Year 2020).
Bork, "Powers and Pitfalls in Sequence Analysis: The 70% Hurdle." Genome Research 10:398-400 (2000).
Bowie et al., "Deciphering the Message in Protein Sequences: Tolerance to Amino Acid Substitutions" Science, 247:1306-1310 (1990).
Burgess et al., "Possible Dissociation of the Heparin-binding and Mitogenic Activities of Heparin-binding (Acidic Fibroblast) Growth Factor-1 from Its Receptor-binding Activities by Site-Directed Mutagenesis of a Single Lysine Residue" J. Cell Biol. 111:2129-2138, (1990).
Christensen et al., "FAM20C-Mediated Phosphorylation of MEPE and Its Acidic Serine- and Aspartate-Rich Motif" JBMRPlus (WOA) 4(8):1-8 (Aug. 2020).
Knee Injury and Osteoarthritis Outcome Score from https://www.physio-pedia.com/KneePInjury_Osteoarthritis_Outcome_Score, pp. 1-8. Accessed Mar. 29, 2020 (Year 2020).
Lazar et al., "Transforming Growth Factor ox: Mutation of Aspartic Acid 47 and Leucine 48 Results in Different Biological Activities" Mol. Cell Biol., 8:1247-1252 (1988).
Li et al., "Subchondral bone in osteoarthritis: insight into risk factors and microstructural changes" Arthritis Research & Therapy, 15:233, pp. 1-12 (2013).
Maheswaran et al. "A Study to Investigate the Osteogenic Potential of Peptide AC-100," EC Orthopaedics, Jan. 31, 2017 (Jan. 31, 2017), vol. 5, Iss. 3, pp. 82-87.
Roemer et al. "An illustrative overview of semi-quantitative MRI scoring of knee osteoarthritis: lessons learned from longitudinal observational studies" Osteoarthritis and Cartilage 24:274e289 275 (2016) (Year: 2016).
Rowe et al. "MEPE has the properties of an osteoblastic phosphatonin and minhibin," Bone, Nov. 26, 2003 (Nov. 26, 2003), vol. 34, Iss. 2, pp. 303-319.
Vincent, G. et al. "Fully Automatic Segmentation of the Knee Joint using Active Appearance Models. Medical Image Analysis for the Clinic: A Grand Challenge." Webpage [online]. Dec. 2009. Retrieved from the internet: <URL.
WOMAC Osteoarthritis Index from https://www.physio-pedia.com/WOMAC_Osteoarthritis_Index, pp. 1-6. Accessed Mar. 29, 2020 (Year: 2020).
Bowes et al. "A Novel Method for Bone Area Measurement Provides New Insights into Osteoarthritis and Its Progression" Annals of the Rheumatic Diseases 2015; vol. 74, pp. 519-525.

\* cited by examiner

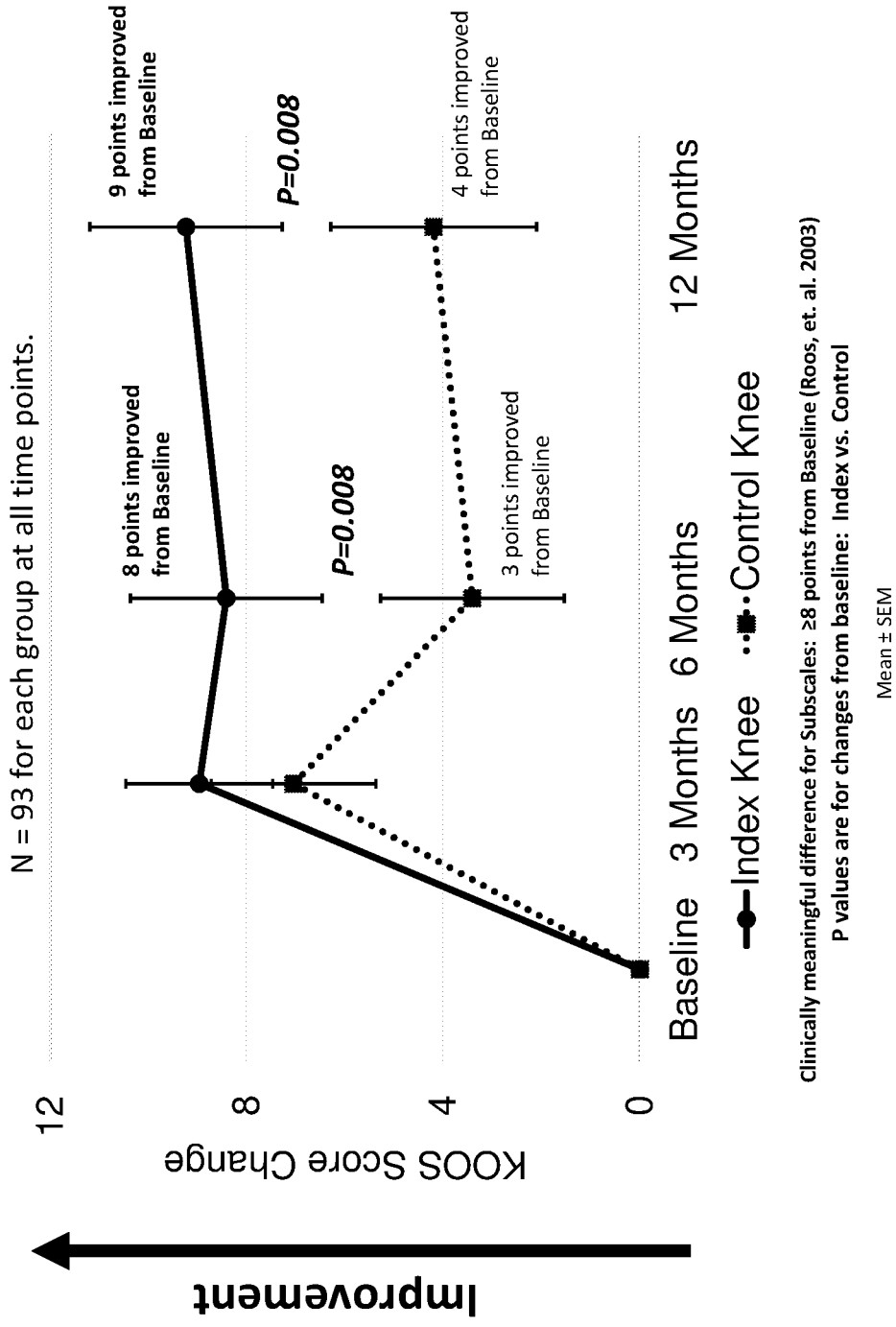

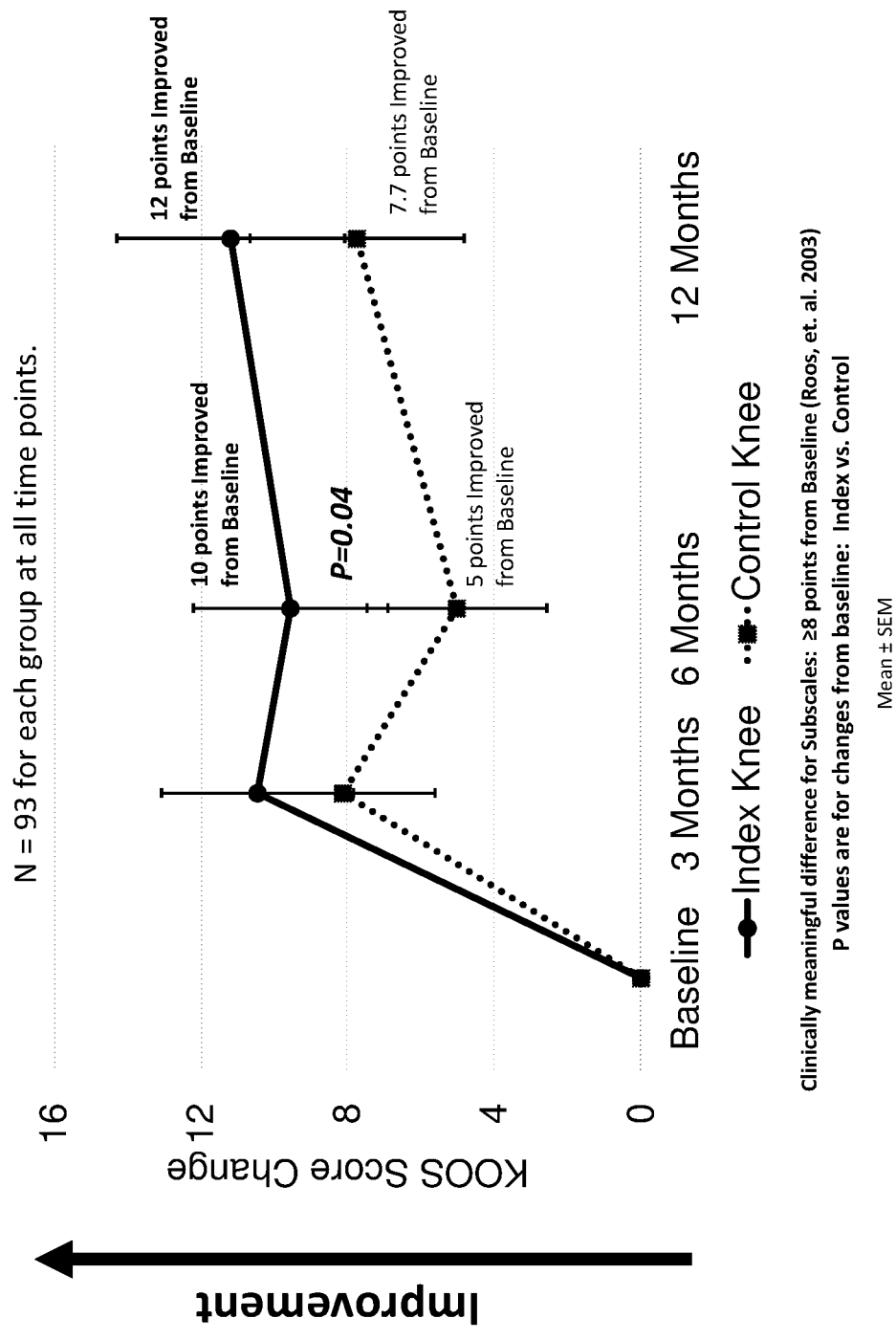
Figure 2. KOOS Knee Function in Sports and Recreation Score Change from Baseline

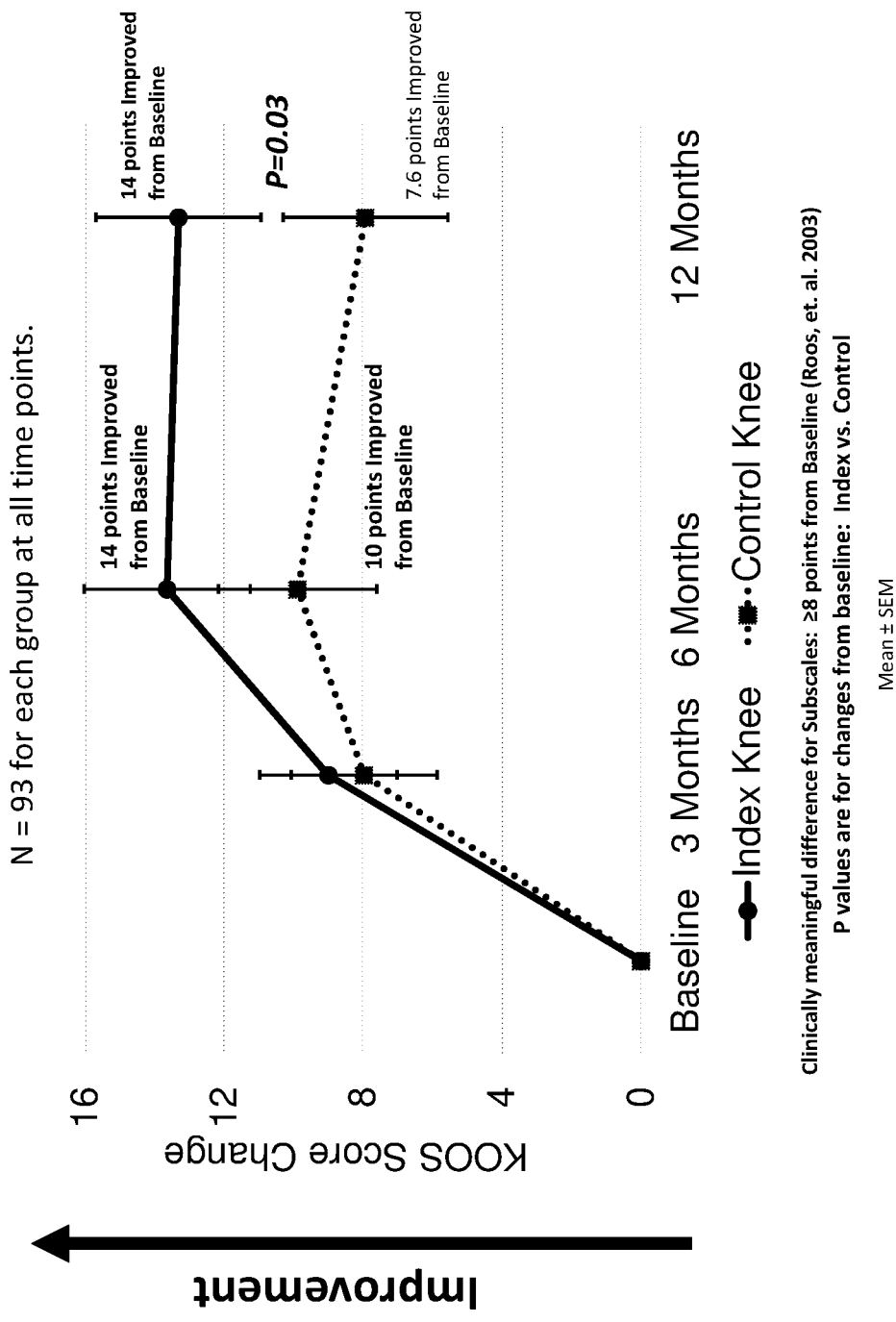

Figure 4. KOOS Pain Questions

1. How often do you experience RIGHT/LEFT knee pain?

Never (0), Monthly (1), Weekly (2), Daily (3), Always (4)

What amount of RIGHT/LEFT knee pain have you experienced the last week during the following activities?

2. Twisting/pivoting on your knee
3. Straightening knee fully moving
4. Bending knee fully
5. Walking on flat surface
6. Going up or down stairs
7. At night while in bed
8. Sitting or lying
9. Standing upright None (0), Mild (1), Moderate (2), Severe (3), Extreme (4)

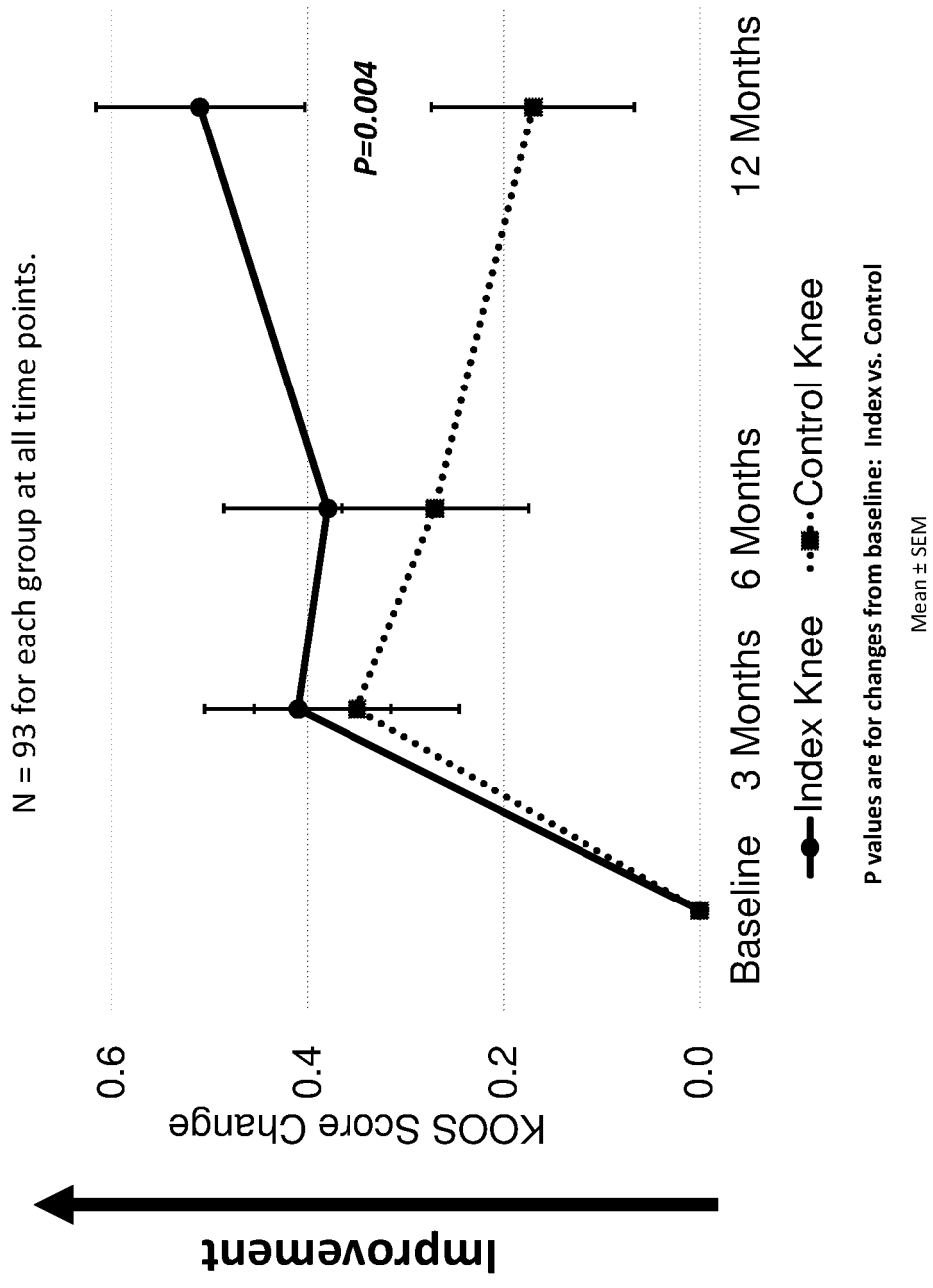

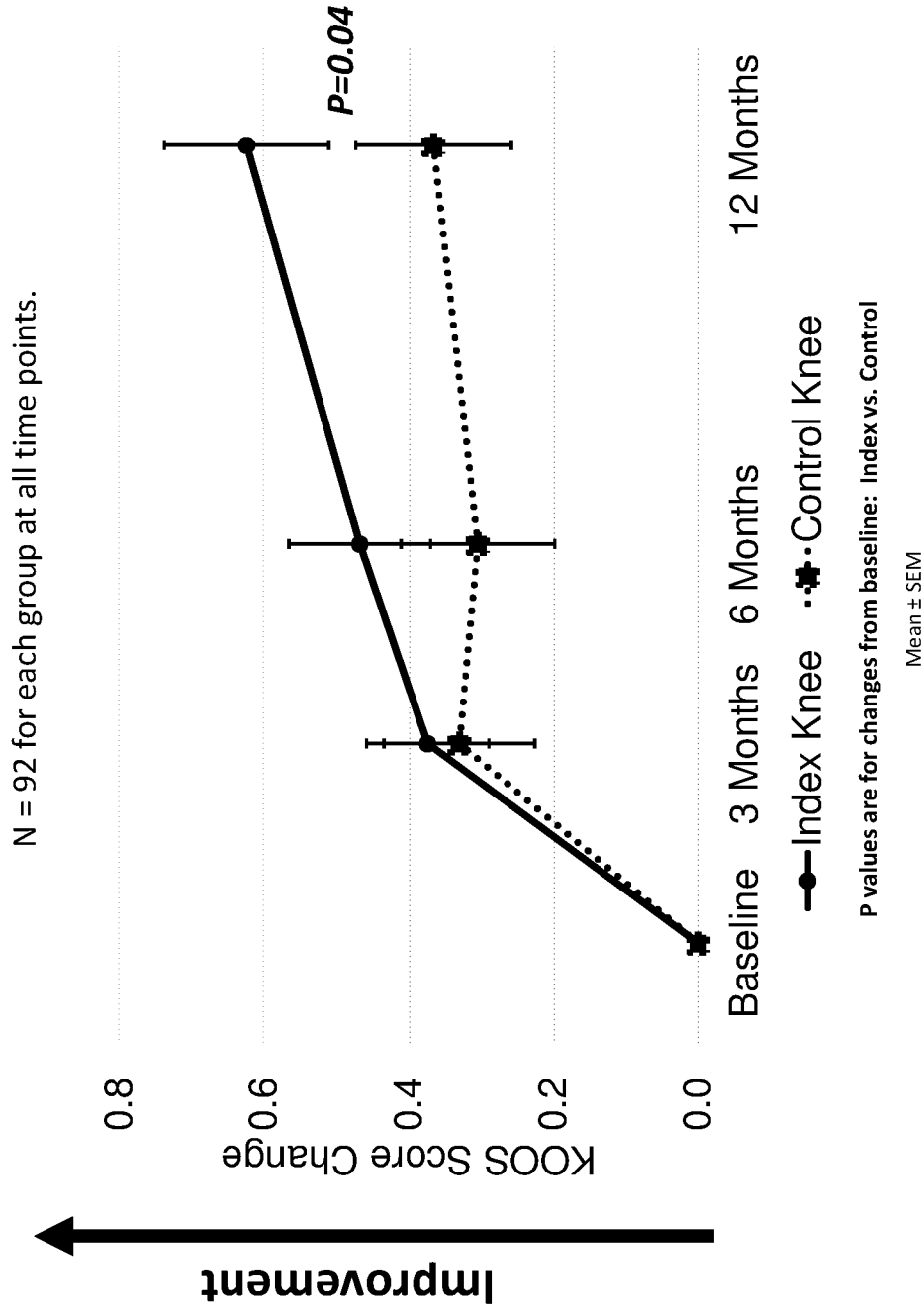

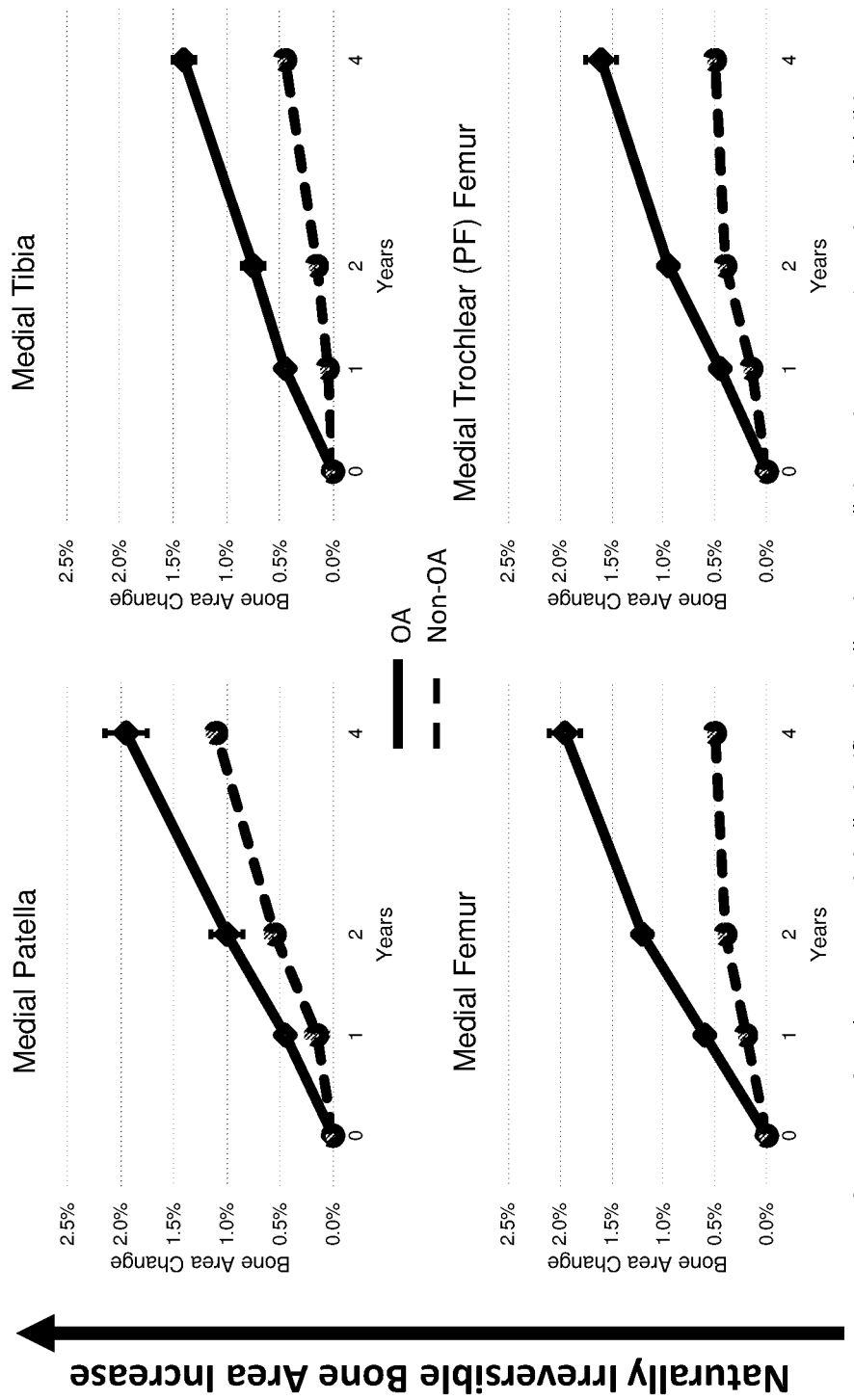
Figure 7. Natural Bone Area Increases: OA vs. non-OA

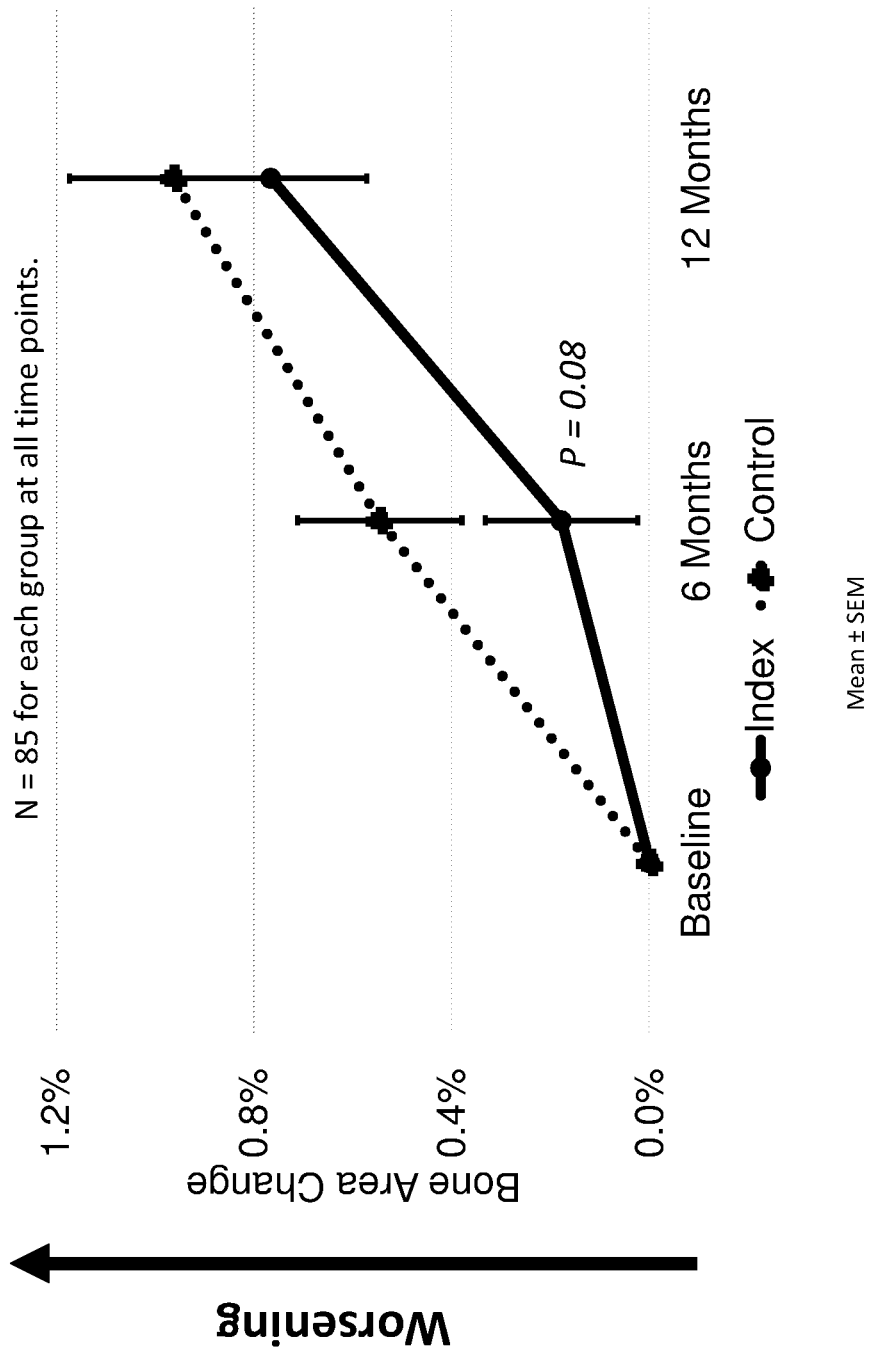

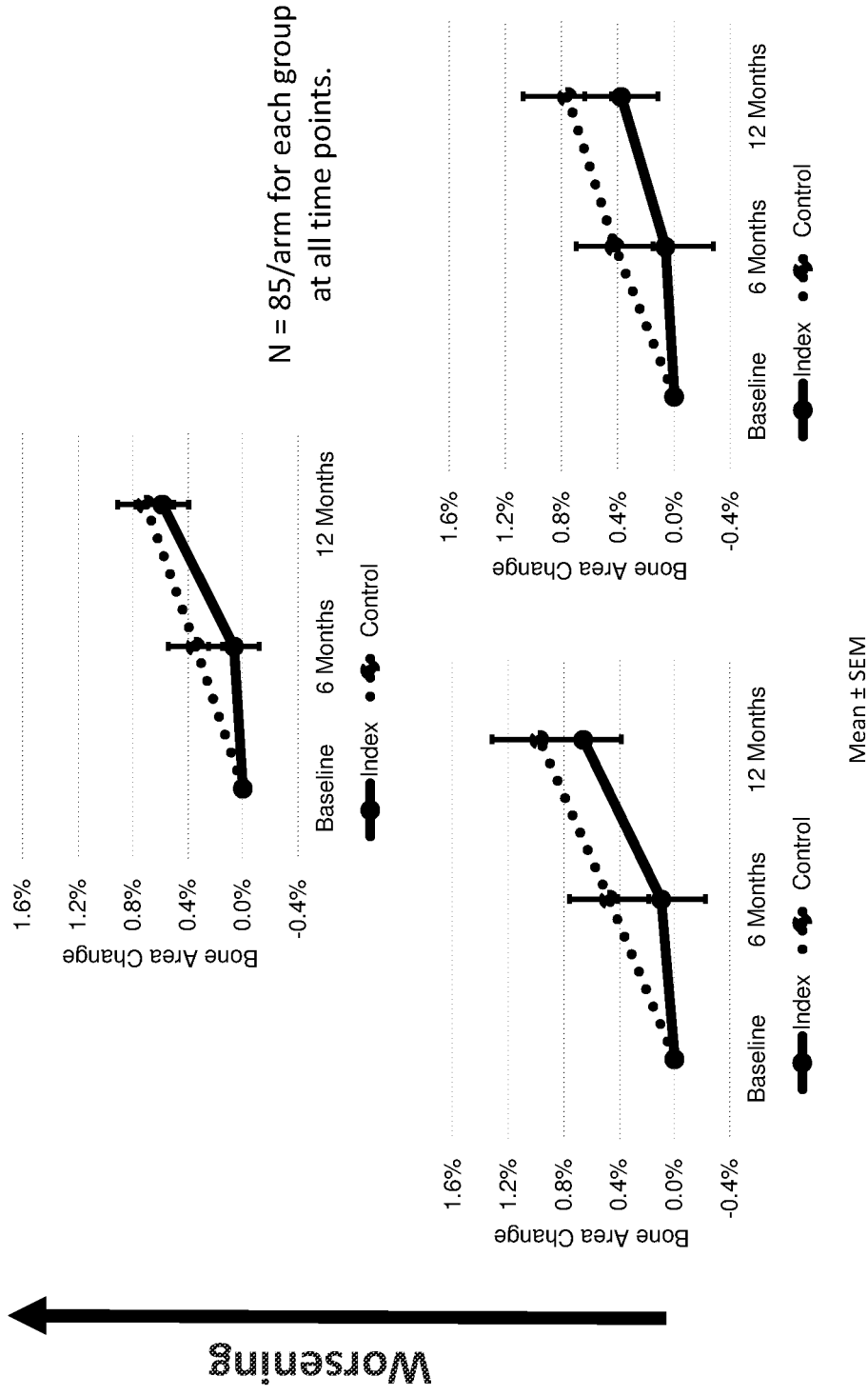
Figure 9. Bone Area Rate of Change in Lateral Femur, Lateral Patella, and Medial Patella

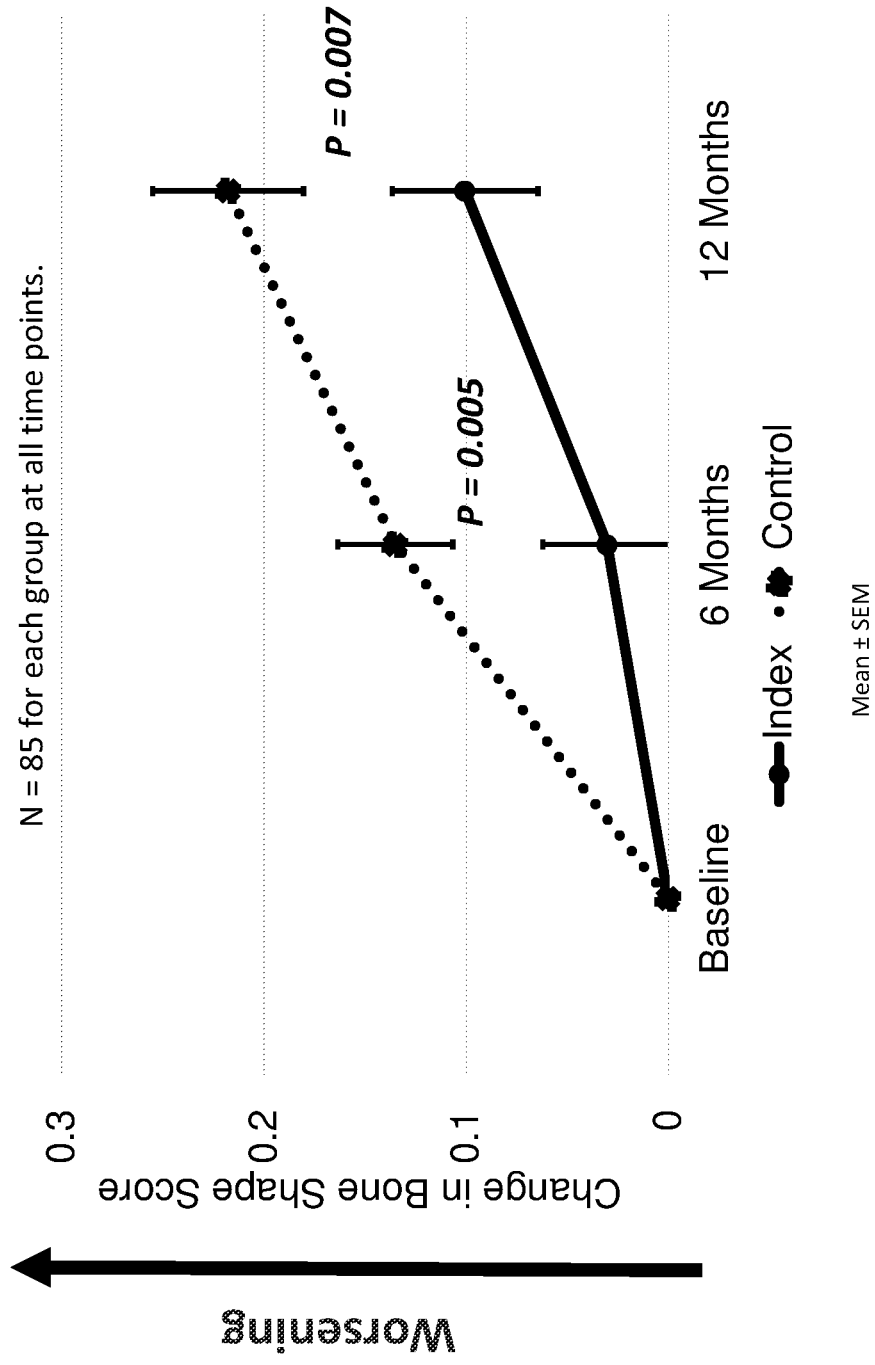

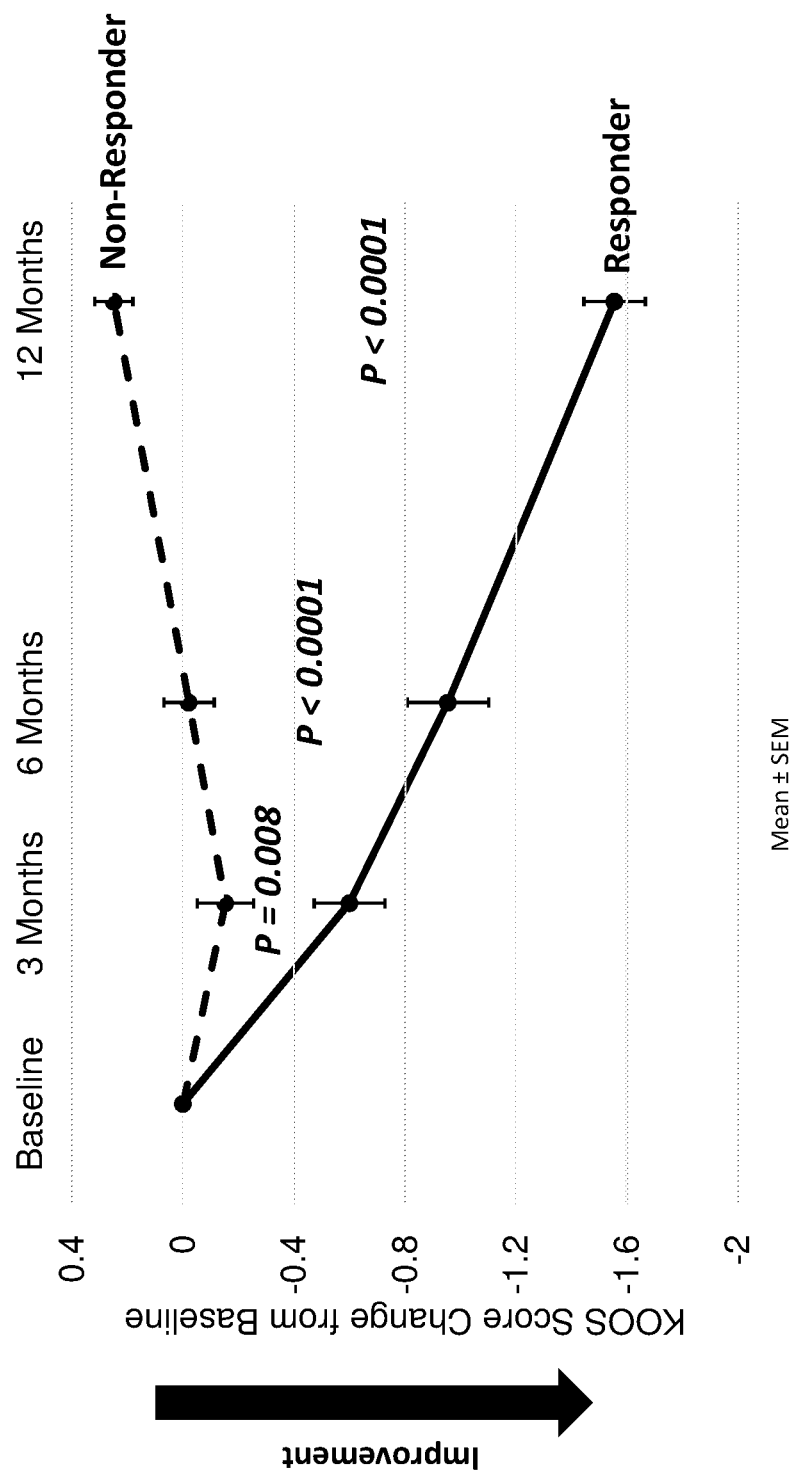
Figure 11. KOOS Pain Frequency: Responder vs. Non-Responder in Index Knees

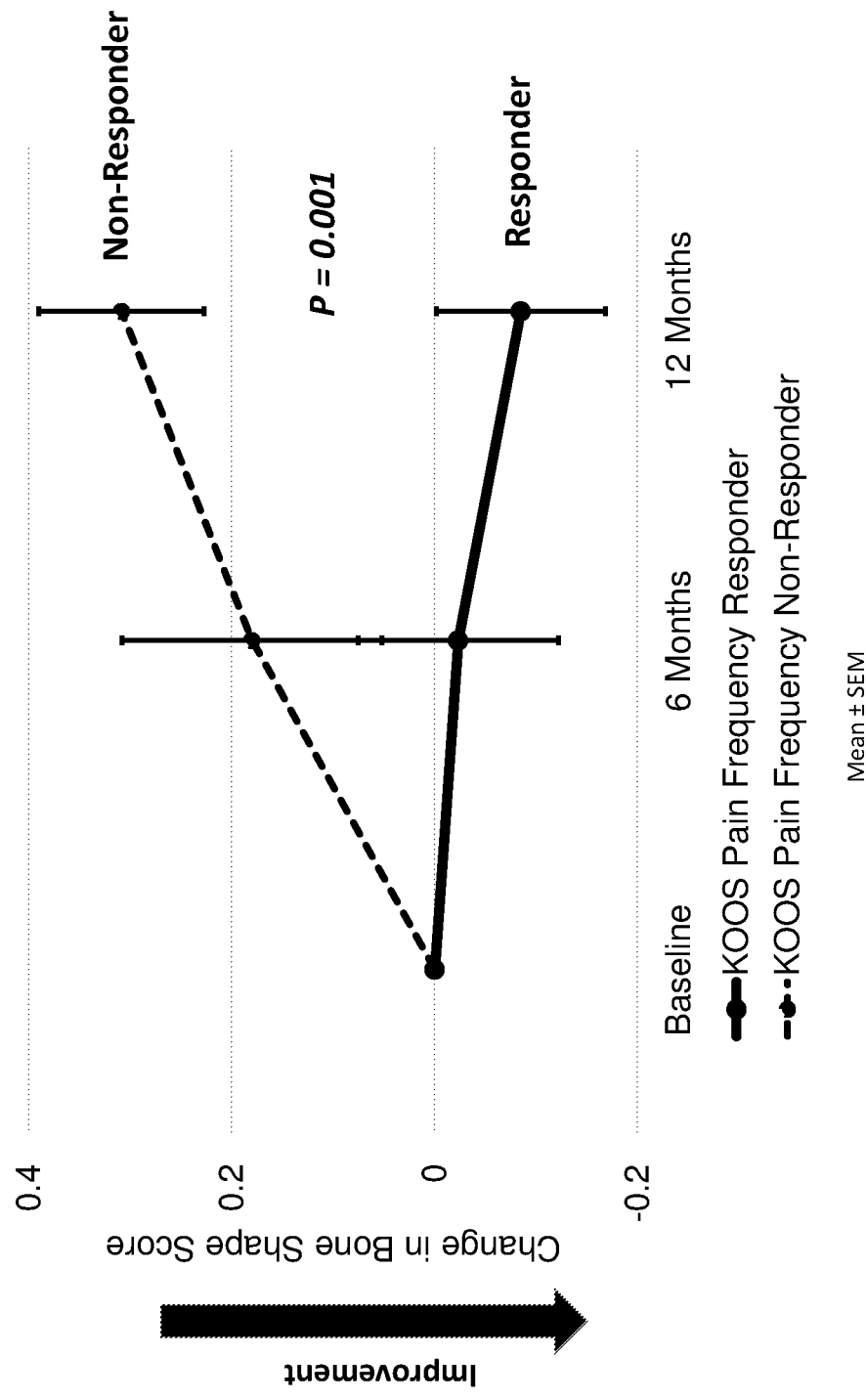
Figure 12. Patella 3D Bone Shape: KOOS Pain Frequency Responder vs. Non-Responder in Index Knees

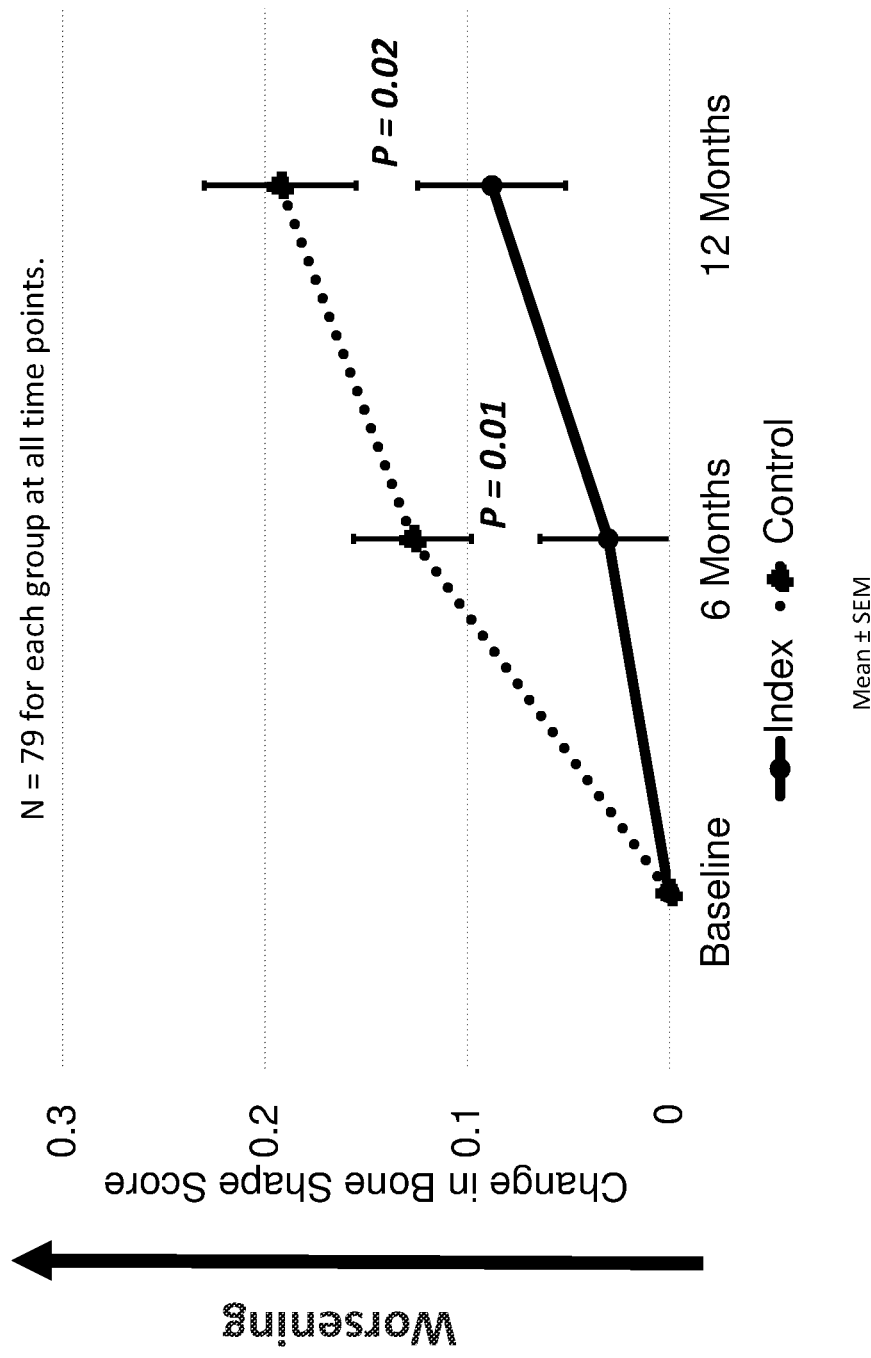
Figure 13. Bone Shape Change in Femur

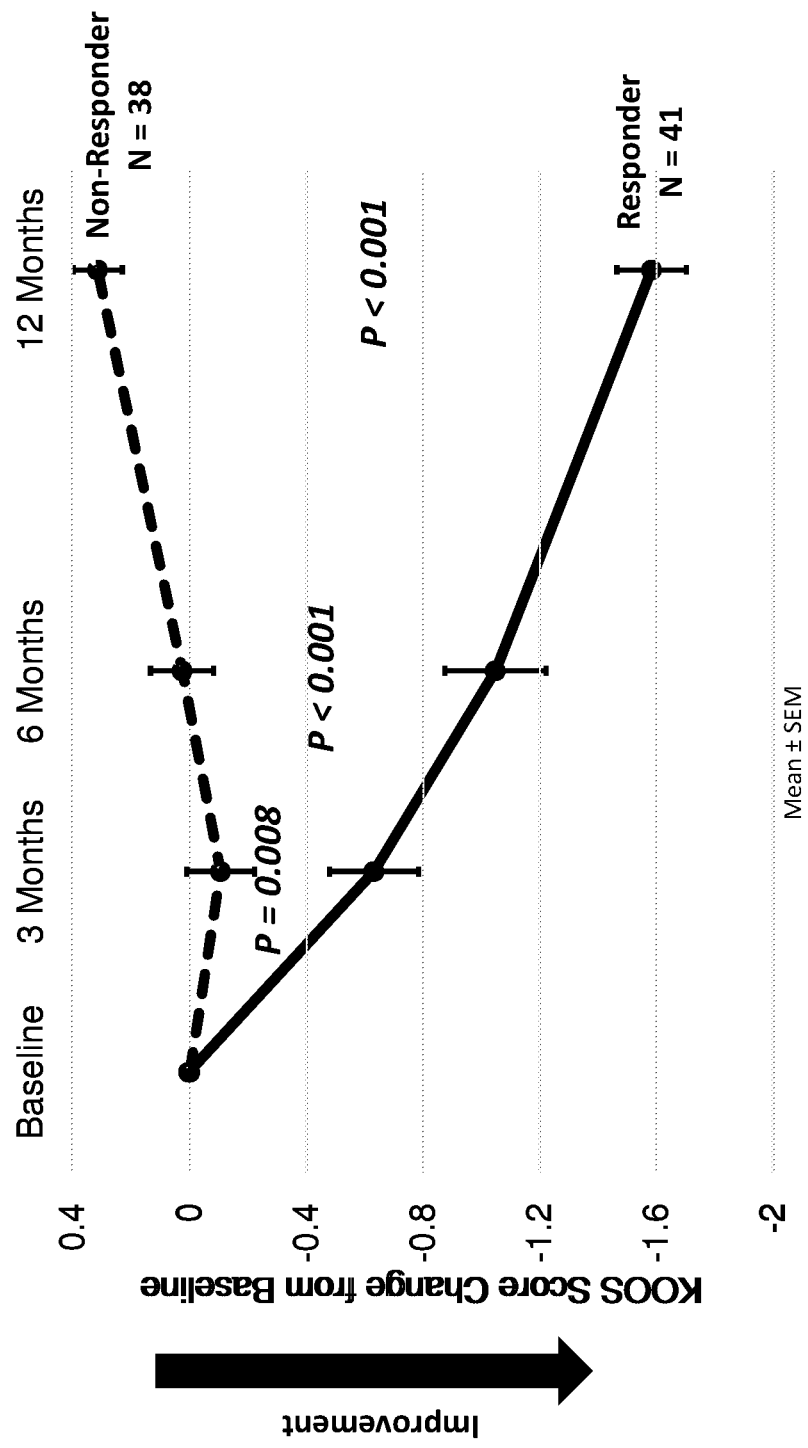
Figure 14. KOOS Pain Frequency: Responder vs. Non-Responder in Index Knees

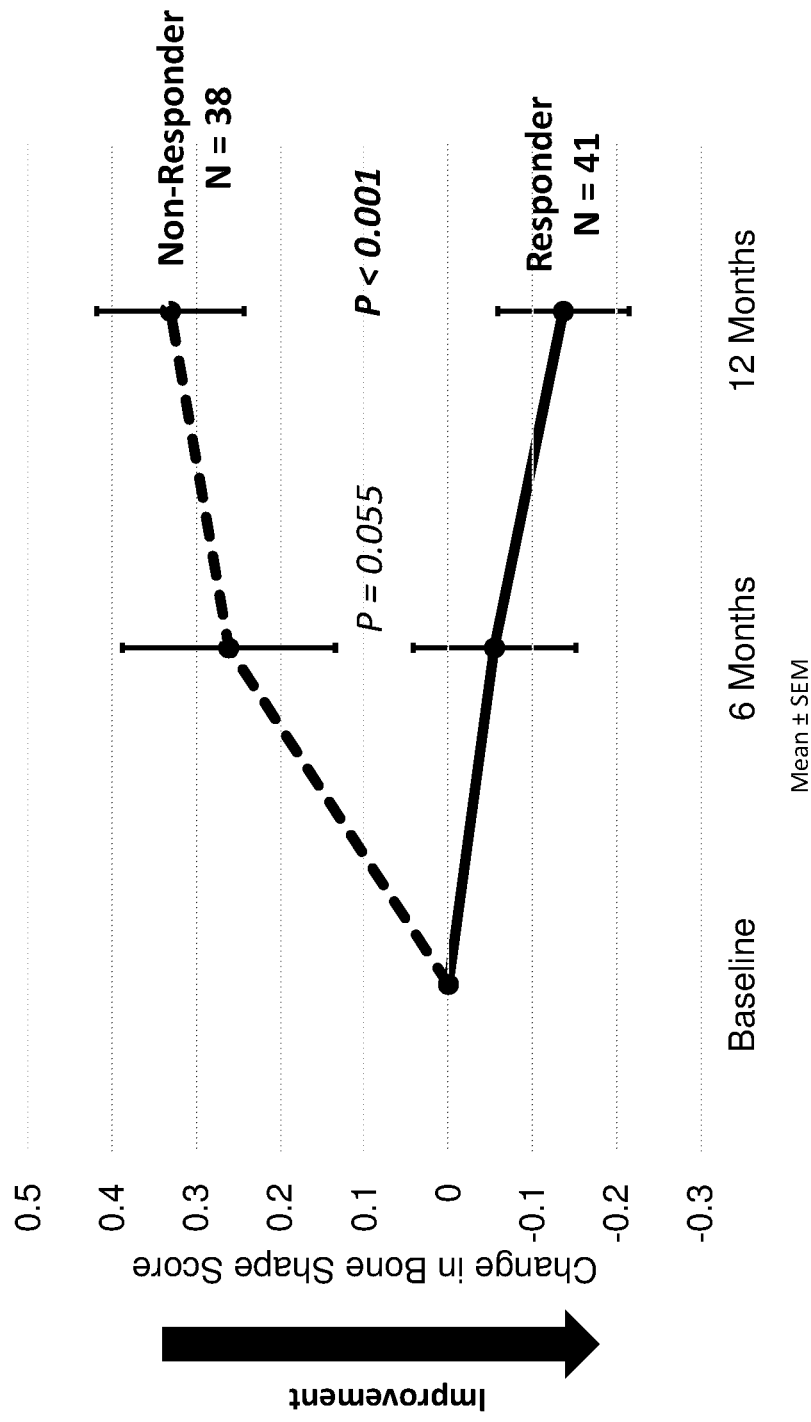
Figure 15. Patella 3D Bone Shape: KOOS Pain Frequency Responder vs. Non-Responder in Index Knees

METHOD OF TREATING OSTEOARTHRITIS

FIELD OF THE INVENTION

The invention relates generally to methods of treating osteoarthritis by modifying joint bone shape change, which is a pathology underlying onset and progression of osteoarthritis.

BACKGROUND

Osteoarthritis

Osteoarthritis is the most common disease of the joints, and one of the most widespread of all chronic diseases. In the US, osteoarthritis (OA) is second only to heart disease as a cause of work disability in men over 50 years of age. Globally, osteoarthritis is the 6th leading cause of years living with disability (Woolf 2003).

Approximately 80% of OA patients need treatment in the knee. Within the knee joint of symptomatic individuals, the most common radiographic pattern is loss of articular (hyaline) cartilage and remodeling of adjacent bone, often with osteophyte formation at the joint margins. Both the tibiofemoral and patello-femoral compartments are commonly affected by degenerative changes. Patello-femoral arthritis due to loss of cartilage in the patella and trochlear groove is common in patients with knee OA, often accompanied by cartilage loss in other joint compartments (Davies 2002).

Pain is a common symptom in patients with knee OA. Pain typically is treated with acetaminophen or non-steroidal anti-inflammatory drugs (NSAIDs). However, further to the initial Boxed Warning and Warnings and Precautions sections of the prescription labels of NSAIDs in 2005, FDA strengthened the existing label warning in 2015 that non-aspirin NSAIDs, including their over-the-counter products, increase the chance of a heart attack or stroke (www.fda.gov/drugs/drug-safety-and-availability/fda-drug-safety-communication-fda-strengthens-warning-non-aspirin-nonsteroidal-anti-inflammatory). Intra-articular treatments using corticosteroids or hyaluronic acid products are also used to reduce pain. Corticosteroid injections have been implicated in further cartilage degeneration in the knees (McAlindon 2017) limiting the willingness of clinicians to use this treatment modality. Corticosteroid injections are not recommended by The American Academy of Orthopaedic Surgeons/American Association of Orthopaedic Surgeons for the treatment of knee OA.

Hyaluronic acid or "viscosupplementation" products are injected into the knee either in once-weekly doses (2 cc) for 3 weeks or in a single administration of a larger dose (6 cc; Chevalier 2010). Injected hyaluronic acid products stay within the joint space briefly, on the order of hours to days. While joint pain reduction may persist for weeks to months in some patients (Cohen 1998), multiple clinical trials have failed to demonstrate a clinically meaningful treatment effect. The American Academy of Orthopaedic Surgeons and American Association of Orthopaedic Surgeons state "We cannot recommend using hyaluronic acid for patients with symptomatic osteoarthritis of the knee." (AAOS Treatment of Osteoarthritis of the Knee Evidence-Based Guideline 2nd Edition, May 18, 2013). (www.aaos.org/cc files/aaosorg/research/guidelines/treatmentofosteoarthritisofthekne-equidel ine.pdf)

Articular Cartilage Degeneration and Current Therapies

It is widely acknowledged that the osteoarthritis involves the progressive degeneration of articular (joint) cartilage. Articular cartilage degeneration in the knee, hip and elbow typically advances slowly with age. Joint degeneration can be accelerated after joint injury or in the setting of chronic or excessive stress on the joints from strenuous physical labor or athletic activities (Sandmark 2000, Felson 1991).

Articular cartilage enables smooth, almost frictionless movement of the joint. It cushions cyclic loads and offsets shear forces on the joint. Articular cartilage is composed of chondrocytes embedded in an extracellular matrix of collagens, non-collagenous proteins, water, and proteoglycans such as aggrecan. Proteoglycans are hydrophilic molecules and enable hydration of the cartilage surface layer. This increases the ability of articular cartilage to buffer biomechanical stress. Articular cartilage is biologically unique and unmatched by any artificially-engineered material or by the fibrocartilage ("scar" cartilage) that forms after injury or microfracture surgery.

Unfortunately, articular cartilage does not regenerate naturally, neither after trauma nor in the setting of chronic "wear and tear" of aging (Buckwalter 2002).

Thus far, only surgical methods and treatments for symptom (pain) management have been approved for patients suffering with knee OA. Surgically, microfracture and abrasion of the bone under the cartilage is used to induce formation of fibrocartilage (scar cartilage). However, fibrocartilage has much less structural strength and stability than normal articular cartilage and degenerates more quickly. Other invasive surgical procedures used for cartilage repair in the knee include drilling into subchondral bone and implanting plugs of cartilage cells (chondrocytes) or their progenitor cells taken from non-weight-bearing parts of the patient's body or from a cadaver (osteochondral autograft/allograft transplantation, OATS procedure). Two surgeries are required, and the patient cannot return to full weight-bearing for approximately 6 weeks after the procedure. Treatment failures are common, as is the need for additional surgery to manage complications.

Two surgical procedures also are required for autologous chondrocyte implantation (ACI), where healthy cartilage is harvested from the knee arthroscopically and grown in culture. The cultured chondrocytes then are implanted. Open-knee surgery is required. The patient's cartilage is cut (debrided) down to the bone and either a periosteal or bioengineered flap is stitched or glued into place. The cultured cells then are injected into the flap. In the Carticel® study of more than 150 patients with ACI, 49% of patients required repeat surgery for complications (Zaslav 2009). Common complications include delamination, graft failure, and disturbed graft fusion (Niemeyer 2008).

The final option for patients with disabling knee OA is joint replacement surgery, an invasive and expensive option with potential for serious morbid complications. Total knee replacement (TKR) of one knee costs $35,000-70,000, which does not include costs of post-operative rehabilitation (at least 6 weeks) and lost productivity. Prosthetic joints have a limited life expectancy and typically must be replaced after 15-20 years; hence TKR is often reserved for older patients. However, average age of the patients who receive TKR has been falling. While that in 2000 was 68, it came down to 65.9 in 2014 (American Academy of Orthopaedic Surgeons 2018). While over 680.000 cases of TKR surgeries were performed in 2014, it is predicted that approximately 1.28 million cases of TKR surgeries (excluding revision surgeries) will be performed in the U.S. in 2030 (American Academy of Orthopaedic Surgeons 2018; aaos-annualmeeting-presskit.org/2018/research-news/sloan tjr/).

Disease Modifying Osteoarthritis Drug (DMOAD)

Understanding the limitations and potential complications of currently available therapies, enormous efforts have been made to develop treatments that slow knee joint degeneration by promote formation of articular cartilage or decreasing cartilage degradation.

For example, several groups have attempted to develop inhibitors of matrix metalloproteinases, which are believed to be responsible for cartilage degradation (Krsezki 2007). Others have attempted to inhibit nitric oxide, believed to accelerate cartilage destruction (Hellio le Graverand 2013). While numerous drugs believed to inhibit cartilage degeneration in knee OA have been tested in controlled clinical trials, thus far none has been successful in slowing or stopping cartilage loss.

Research in cartilage regeneration represents an alternative approach to knee OA. A variety of growth factors have been tested for efficacy in cartilage regeneration, including the TGFβ (Transforming Growth Factor β) family molecules such as Bone Morphogenetic Protein-7 (BMP-7). None of the growth factors studied thus far have shown efficacy in clinical trials (Guermazi 2017). While Fibroblast Growth Factor-18 (FGF-18, a.k.a., Sprifermin) demonstrated a small but statistically significant increase in tibiofemoral cartilage thickness in subjects with knee OA, active treatment failed to show improvement in subjects' knee function or pain when compared with placebo (Hochberg 2017, Hochberg 2018).

Drugs under development that may regenerate articular cartilage or delay its degeneration are regarded as potential Disease Modifying Osteoarthritis Drugs (DMOADs).

TPX-100, a peptide of SEQ ID No. 1, has demonstrated articular cartilage formation activity in the goat model of cartilage injury, and is a candidate DMOAD (U.S. Pat. Nos. 7,888,462 and 8,426,558). The peptide of SEQ ID No. 1 has been tested in a randomized, double-blind, placebo-controlled trial of subjects with bilateral knee OA. TPX-100-treated knees demonstrated statistically significant and clinically meaningful improvements in knee function as well as in other clinical outcomes compared to placebo-treated knees (McGuire 2017). Knee functional improvement in TPX-100-treated knees was robust and was sustained through the end of the year-long study. Knee's functional improvement was associated with increase or stabilization of tibiofemoral cartilage thickness at 12 months, as measured by MRI (McGuire 2018).

Questions on Cartilage Structure in Osteoarthritis Pathophysiology

Articular cartilage degeneration has been believed to be the primary pathologic mechanism of knee OA. However, clinical observations have led some researchers to question whether cartilage degeneration may follow changes in other parts of the joint.

For example, with severe loss of articular cartilage, the underlying bone is exposed. It would be reasonable to expect this "bone-on-bone" arthritis to be associated with severe pain, given the dense innervation of bone with pain fibers. However, it is not uncommon for subjects with knee OA to have little or no pain, despite complete loss of cartilage revealed on imaging. On the other hand, many OA patients experience severe pain and functional limitations when their articular cartilage has little measurable degeneration.

The discrepancy between clinical symptoms and changes in cartilage thickness has been demonstrated in studies of the candidate DMOAD FGF-18 (a.k.a. Sprifermin), a putative chondrocyte growth factor. In a clinical trial of over 500 subjects with knee OA, four FGF-18 dosing groups were compared with a placebo group. Subjects received three, once-weekly intra-articular injections (i.e., days 0, 7, and 14) of FGF-18 or placebo. The series of active drug or placebo injections was repeated at months 6, 12, and 18. Interval changes in tibiofemoral cartilage thickness were measured by MRI, and clinical outcomes were measured by the Western Ontario and McMaster Universities Osteoarthritis Outcome Score (WOMAC), a validated patient-reported outcome measure. At 24 months, the FGF-18-treated groups demonstrated dose-dependent increases in tibiofemoral cartilage thickness compared with the placebo group. The differences in cartilage thickness reached statistical significance in the two highest dose groups compared to the placebo-exposed group. However, no difference in clinical benefit was detected in any treatment group when compared with placebo (Hochberg 2017). At 36 months, FGF-18 treated groups also failed to demonstrate clinical benefit compared with the placebo-treated group (Hochberg 2018).

A draft guideline for development of DMOADs for knee OA was first issued by the U.S. Food and Drug Administration in 1999, in which an increase in joint space width or delay in narrowing of the joint space as measured by X-ray represented a potentially acceptable endpoint for drug approval. However, this draft guideline was replaced in August 2018, in which the FDA concludes that neither X-ray nor other imaging can be recommended as a surrogate marker for efficacy in DMOAD development. The latest guideline is brief, and states:

". . . there are several ongoing issues with developing such products, including the multifactorial and complex etiopathogenesis of the disease, the well-recognized discordance between structural changes and signs/symptoms/function, the lack of standard definitions of disease progression, and, correspondingly, the absence of endpoints to reliably assess the ability of a product to alter OA disease progression." (FDA 2018)

In summary, it is now generally recognized that the relationship between changes in cartilage thickness and clinical outcomes is non-obvious. Specifically, changes in cartilage thickness may not be sufficient to explain the disease of OA as patients experience it; nor can cartilage thickness increases be assumed to modify clinical outcomes of OA unless they are persuasively linked to patient benefit.

Pathological Role of Subchondral (Periarticular) Bone in Knee Osteoarthritis

The bones underlying articular cartilage are being studied to elucidate their role in onset and progression of OA.

Therapeutic agents used to treat osteoporosis such as strontium ranelate (Reginster 2013), calcitonin (Karsdal 2015), and zolendronate (Laslett 2012) have been clinically tested as potential treatments for OA. These agents promote new bone formation or inhibit bone resorption. Their efficacy in stabilizing or strengthening subchondral bone has not been demonstrated clinically, and significant adverse effects have dampened enthusiasm for these agents. For example, strontium ranelate was found to increase the risk of myocardial infarction and its use has been limited by the European Medicines Agency.

A recently proposed marker of OA progression is measurement of the three-dimensional (3D) change in periarticular bone shape. In a comparison of a large population of subjects from the National Institutes of Health Osteoarthritis Initiative (OAI) database, knees with radiographic OA demonstrated increasing periarticular bone area over time in all subjects with OA compared with normal controls. Changes in bone area have been shown to predict OA symptom progression and joint failure better than changes in cartilage thickness or decreases in joint-space width (Bowes 2015).

3D analyses of changes in periarticular bone shape among subjects from the OAI have revealed a consistent, unidirectional pattern associated with progression of OA. Flattening of bone shape occurs in femur, tibia and patella even in the absence of marked cartilage loss. The 3D shape change of periarticular bones can be measured using multiple anchor points ("principal components") that are defined on the bone surface. The shift in position of these anchor points over time is measured on MRI images and analyzed algorithmically using active appearance modelling (AAM). As OA progresses, the bone shape, particularly in the periarticular surfaces of the femur, changes in a predictable fashion in subjects, regardless of demographic differences such as age, gender and body mass index. In the non-OA joints from the OAI database, defined as those with Kellgren-Lawrence (KL) scores of 0, reflecting no OA by X-ray criteria, the rate of the periarticular bone shape change over 4 years is significantly slower than that in OA joints evaluated by KL criteria. Bone shape change is normalized to a "B Score", representing the extent of bone shape change in terms of standard deviations from the range of periarticular shape changes in knees unaffected by OA (Neogi, 2013; Hunter 2016).

Changes in 3D periarticular bone shape better predict knee OA pain progression than semi-quantitative analyses of bone marrow lesions (Dube 2018).

The effects of bisphosphonate treatment on knee OA was evaluated using bone area measurement and 3D shape change assessments among subjects from the OAI database who were receiving treatment for osteoporosis. Bisphosphonate users showed a statistically significant reduction in bone area increase in the medial tibia as compared to non-bisphosphonate users; however, there were no differences in 3D bone shape change over time between the groups. No analysis of differences in symptoms of knee OA such as function or pain was reported (Haj-Mirzaian 2018).

There have been epidemiology reports that high bone mass or high bone mineral density is associated with increased risk of knee OA or joint replacement (Nevitt 2010, Hardcastle 2013). Combining these with the bisphosphonate data above, bone mass increase or strengthening does not necessarily improve or reduce the risk of OA.

TPX-100 Peptide

TPX-100 is a synthetic peptide consisting of 23 amino acids with amino acid sequence of TDLQERGDNDIS-PFSGDGQPFKD (SEQ ID No. 1), derived from human Matrix Extracellular Phosphoglycoprotein, or MEPE.

The TPX-100 drug substance has been manufactured as acetate and sodium salts, respectively, and the final formulation in either case is lyophilized powder with the C-terminus amidated. The TPX-100 injection (drug product) used in the clinical study was formulated in water for injection.

TPX-100 has been shown to promote tissue-appropriate regeneration of dentin, bone, and cartilage without any soft tissue calcification or ossification. TPX-100 can be administered by conventional methods such as subcutaneous or intra-articular injection.

In non-clinical safety and efficacy studies, TPX-100 was first tested for its bone formation activity. TPX-100 peptide was identified as a "bone formation active site" of human MEPE, demonstrating thickening of cultured neonatal mouse calvaria (Hayashibara 2004). Subsequently, TPX-100 administered by subcutaneous injection demonstrated acceleration of bone fracture healing in a widely-used rat long bone fracture model (a.k.a., Einhorn model) (Lazarov 2004). In addition, as a part of early studies of the TPX-100 peptide, it was also found to promote dentin formation in a rat dental defect model (Six 2007). TPX-100 was well tolerated in these in vivo bone formation and dentin formation studies. Safety of the TPX-100 peptide was further confirmed in multiple GLP toxicology studies and a Phase 1 clinical study with healthy volunteers.

Based on these safety and bone and dentin formation data, TPX-100 was tested in two Phase 2 studies for alveolar bone and dentin formation activities, respectively. TPX-100 was well tolerated in both studies. One of the studies testing dental activities demonstrated reparative dentin formation by TPX-100 administered in the defects in human molar (Lazarov 2006). The other study testing alveolar bone formation did not show a difference between drug vs. placebo-exposed groups.

It should be noted that in these non-clinical and clinical studies investigating TPX-100 efficacy on bone and/or dentin, there were neither data nor observations that indicated or suggested that TPX-100 affects these hard tissues in terms of their shape or other morphological features. TPX-100 demonstrated only repair of flat and thin bone or dentin by increase in these hard tissues, and, in a rodent model, healing of experimental fractures located in the central region of a long bone.

Cartilage regeneration properties of TPX-100 subsequently were demonstrated in the goat model using standardized large cartilage defects. In a full-thickness chondral defect model in ambulatory goats, a regimen of four weekly intra-articular (IA) injections of TPX-100 (125 mg and 250 mg) was associated with statistically significant, histologically-confirmed hyaline cartilage regeneration at 6 months post-surgery compared to cartilage regeneration in the vehicle control group. The drug was safe and well-tolerated in these freely weight-bearing, ambulatory animals (U.S. Pat. Nos. 7,888,462 and 8,426,558).

A randomized, double-blind, placebo-controlled clinical study of TPX-100 was performed in patients with mild to severe bilateral knee osteoarthritis. It was anticipated that TPX-100 would improve critical knee functions affected by knee OA.

In this clinical study, test articles were administered by once-a-week intra-articular (IA) injections four times over three consecutive weeks (Days 0, 7, 14, and 21). TPX-100 was safe and well tolerated in this study.

TPX-100-treated (Index) knees demonstrated clinically meaningful and statistically significant improvement in knee function in daily living activities ("ADL") and in sports and recreational activities ("Sports and Recreation") as measured by the Knee injury and Osteoarthritis Outcome Score (KOOS), Clinically meaningful and statistically significant improvements also were demonstrated in knee-related quality of life ("Knee-related QOL") and pain going up or down stairs. In addition, significant improvements in favor of Index knees were demonstrated in "Function" and "Total" scores as measured by the Western Ontario and McMaster Universities Osteoarthritis Score (WOMAC). The improvements in TPX-100-treated knees were observed at 6 or 12 months, or both. In terms of overall cartilage thickness change from baseline to 6 or 12 months, Index and Control Knees were not measurably different on MRI. However, among TPX-100-treated "responder" knees, those with clinically meaningful functional improvements, tibiofemoral (TF) cartilage thickness significantly increased from baseline to 12 months (McGuire 2018).

As described above, TPX-100 was derived from human MEPE. Several other orthologues of MEPE have been known, and thus, the orthologues of TPX-100 are also known. The examples of the TPX-100 orthologues are as follows:

TDLQERGDNDMSPFSGDGQPFKD (Macaque) (SEQ ID No. 2)

PDLQERGDNDISPFSGDGQPFKD (Canine) (SEQ ID No. 3)

PDLQGRGDNDLSPFSGDGPPFKD (Taurus) (SEQ ID NO. 4)

PDLLVRGDNDVPPFSGDGQHFMH (Rat/Mouse) (SEQ ID No. 5)

The amino acid sequence of rat/mouse orthologue has the least homology to that of human orthologue (15/23 identical, 65% homology). Since the rat orthologue is known to promote tritium-thymidine incorporation by human osteoblastic mesenchymal stem cells (U.S. Pat. Nos. 7,888,462 and 8,426,558), it should be reasonable to assume that these orthologues and their analogues have common biological functions to those of TPX-100. These peptides contain a common amino acid sequence of DLXXRGDNDXXPFSGDGXXF (SEQ ID No. 6), where X can be any amino acid.

SUMMARY OF THE INVENTION

A novel method of treating osteoarthritis (OA) is presented. The method comprises any therapeutic intervention that can delay, arrest, or reverse pathological changes of three-dimensional (3D) periarticular bone shape associated with disease onset and progression. This marks the first time that therapeutic intervention of pathological periarticular bone shape change was demonstrated and shown to correlate significantly with striking improvements in numerous disabling symptoms of knee OA.

An aspect of the invention is a method of modifying the pathological change of three-dimensional (3D) periarticular bone shape by administration (which may be by local injection) to a patient (which may be a human diagnosed with osteoarthritis) a formulation of the peptide of SEQ ID No. 1 in a therapeutically effective amount.

Another aspect of the invention is treating OA by delaying, arresting or reversing periarticular bone shape changes where the method includes diagnosing the periarticular bone shape of the affected joint by MRI-based 3D shape analysis of the joint, administering to the patient a formulation comprised of therapeutically effective amount of peptide of SEQ ID No. 1, and measuring the periarticular bone shape change after a period such as 6 months, 12 months, 24 months, etc. to determine whether or not the bone shape was significantly changed as compared to the one prior to the drug treatment.

Bone shape analysis by an alternative imaging technology may be used, e.g., using joint images obtained by computerized tomography, ultrasound or other imaging modalities.

MRI commonly is used to diagnose features of osteoarthritis such as articular cartilage thinning or meniscal pathology. Bone shape before and after treatment can be analyzed using image sequences acquired for evaluation of cartilage. Combining bone shape and cartilage analyses could increase the sensitivity of evaluation of treatment effects of a therapeutic intervention.

The peptide is formulated into an injectable formulation that can include water or saline and can be injected locally into the knee by intra-articular or subcutaneous routes. Several orthologues and analogues of the peptide of SEQ ID No. 1 are known to show similar activities to that of the peptide of SEQ ID No. 1. Any one of those peptide can be used by formulating them into an injectable formulation including water for injection, saline, and the like.

In an aspect of the invention, the method is carried out with the injection being administered only once, only twice, three times, four times, five times, etc. The dosing may be delivered daily, every three days, once a week, every ten days, once a month, once every other month, once a quarter, semiannually, once a year, or in different combinations thereof.

In an aspect of the invention, the method includes follow up evaluation of the patient's knee function and/or pain using instruments such as the KOOS and/or WOMAC scales. The evaluation may also be carried out based on other appropriate patient reported outcomes (PROs) and by clinical evaluation.

In an aspect of the invention, the dosing may be in a range of from 50 mg to 500 mg, or 100 mg to 400 mg, or 200 mg, wherein all milligram doses are ±20%, ±10%, ±5%.

In an aspect of the invention, the patient is first evaluated based on inclusion and exclusion criteria as described herein.

In an aspect of the invention, joint aging is delayed, arrested, or reversed by modifying an inevitable age-associated periarticular bone shape change.

An aspect of the invention includes a method and/or use of a compound in order to impact the shape change of a bone underlining articular cartilage in a patient which may be any animal but includes humans and canines which method or use comprises locally injecting into a joint of a patient a therapeutically effective amount of a formulation in an injectable carrier which formulation includes a peptide sequence of any of the SEQ ID NOs.: 1, 2, 3, 4, 5, and 6. The injecting may be intra-articular and the injecting may be repeated as needed (PRN) or repeated weekly over a period of two, three, four or more weeks with the injecting including the peptide in an amount in a range of 50-400 mg±20% with the treatment continuing in order to impact the shape change of a bone underlining articular cartilage in the patient whereby shape change of the bone is impacted wherein the shape change may be in a patient diagnosed with osteoarthritis.

An aspect of the invention includes the method and/or use as described above wherein the dosing amounts are adjusted based on a number of factors including the size, weight, sex, and condition of the patient. In addition, dosing amounts are based on the species of the patient such as human or canine, and the particular joint being treated. Larger patients and larger joints require larger doses and smaller patients and smaller joints require smaller doses. The basic concept of the invention is not limited by a particular dosing range as those skilled in the art will understand that dosing amounts vary depending on factors as described above as well as other factors to be taken into consideration. The specific dosing amounts described above are preferred dosing ranges for an average adult human knee. Those skilled in the art can extrapolate from the dosing amounts to provide other dosing ranges for other joints and/or animals.

An aspect of the invention includes the method and/or use as described above wherein the sequence is a sequence of SEQ ID NO.:1 and the patient is a human or a dog. The injection may be intra-articular and the bone shape change may be due to either osteoarthritis or aging.

Another aspect of the invention comprises the method and/or use as described above wherein dosing and/or further treatment is determined at least in part by obtaining images before and/or during treatment and comparing images to determine impact of bone shape due to the injecting, wherein the measuring and remeasuring may be carried out using active appearance model (AAM) software.

BRIEF DESCRIPTION OF THE DRAWINGS

The invention is best understood from the following detailed description when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 1 is a graph showing the results of an actual clinical study in which changes in knee function from baseline through 12 months are indicated as measured using the Activities of Daily Living subscale of the Knee injury and Osteoarthritic Outcome Score ("KOOS ADL").

FIG. 2 is a graph showing the results of an actual clinical study in which changes in knee function from baseline through 12 months are indicated as measured using the Sports and Recreation activities subscale of KOOS ("KOOS Sports and Recreation").

FIG. 3 is a graph showing the results of an actual clinical study in which changes from baseline through 12 months are indicated as measured using the Knee-Related Quality of Life subscale of KOOS ("KOOS Knee-Related QOL").

FIG. 4 shows the questions and scoring systems for KOOS Pain subscale.

FIG. 5 is a graph showing the results of an actual clinical study in which changes from baseline through 12 months are indicated as measured using the component of the KOOS Pain subscale that specifically addresses "Pain going up or down stairs".

FIG. 6 is a graph showing the results of an actual clinical study in which changes from baseline through 12 months are indicated as measured using the component of the KOOS Pain subscale that specifically addresses frequency of knee pain.

FIG. 7 contains graphs showing the results of an actual clinical study in which differences in the rates of change of periarticular bone area in OA vs. non-OA knees in four regions of knee joint are exhibited.

FIG. 8 is a graph showing the results of an actual clinical study in which changes in the periarticular bone area of the medial femur from baseline through 12 months are indicated.

FIG. 9 contains graphs showing differences of rate of change of periarticular bone area in three regions in Index (TPX-100-treated) and Control (placebo-exposed) Knees.

FIG. 10 is a graph showing the results of an actual clinical study in which changes in the bone shape score of the femur from baseline through 12 months are indicated.

FIG. 11 is a graph showing the results of an actual clinical study in which changes in pain frequency from baseline through 12 months are indicated comparing responders vs. non-responders to active treatment with the peptide of SEQ ID No. 1.

FIG. 12 is a graph showing the results of an actual clinical study in which 3D bone shape changes in the patella from baseline to 12 months are correlated to pain frequency in responders vs. non-responders to active treatment with the peptide of SEQ ID No. 1.

FIG. 13 is a graph showing the results of an actual clinical study in which 3D bone shape of the femur from baseline through 12 months are indicated.

FIG. 14 is a graph showing the results of an actual clinical study in which changes in pain frequency from baseline through 12 months are indicated comparing responders vs. non-responders to active treatment with the peptide of SEQ ID No. 1.

FIG. 15 is a graph showing the results of an actual clinical study in which 3D bone shape changes in the patella from baseline to 12 months are correlated to pain frequency in responders vs. non-responders to active treatment with the peptide of SEQ ID No. 1.

DETAILED DESCRIPTION OF THE INVENTION

Before the present methods, uses and formulations are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an injection" includes a plurality of such injections and reference to "the measurement" includes reference to one or more measurements and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Cartilage Structure in Osteoarthritis Pathophysiology

As described in the Background section above, a long-held interpretation of the pathogenesis of osteoarthritis (OA) has been degeneration of joint (articular) cartilage, which was believed to result in disfunction and pain in the affected joint. Multiple candidates for a DMOAD have been tested in clinical trials to target articular cartilage structure modification. However, very few have actually demonstrated any cartilage structure modification in human clinical trials. Even when small cartilage increases were observed in clinical studies, no corresponding patient benefit, such as knee function or pain improvement, was observed when compared with placebo.

The only published clinical data to date that demonstrated an association between cartilage thickness increase/stabilization and statistically significant clinical improvement in knee OA patients are the results of the randomized placebo-controlled study of the peptide of SEQ ID No. 1 (McGuire 2018).

Efficacies on Clinical Benefits and Cartilage Thickening in Osteoarthritis Knees The peptide of SEQ ID No. 1 (a.k.a., TPX-100) has been known to promote new cartilage formation (See U.S. Pat. Nos. 7,888,462 and 8,426,558).

For this activity, the peptide of SEQ ID No. 1 was tested for its clinical safety and efficacy on a condition involving cartilage damage in a Phase 2 randomized double-blind placebo-controlled clinical trial with mild to severe knee osteoarthritis (OA) patients. See EXAMPLES.

The anticipated clinical benefit of the peptide was improvement of knee function. Better joint function could be anticipated if the peptide repairs damaged cartilage, maintains viable cartilage, and/or makes cartilage more resilient to the wear-and-tear of aging.

Knee functions measured by KOOS ADL and WOMAC Function subscales demonstrated clinically meaningful and statistically significant ($p=0.008$) improvement in the knees treated with the peptide of SEQ ID No. 1 ("Index Knee") as compared to the placebo-treated knees ("Control Knee") at both 6 and 12-month time points after treatment. See FIG. 1.

Index Knees also showed clinically meaningful and statistically significant improvements in Sports and Recreation and Knee-Related QOL subscales of KOOS as compared to Control Knees. See FIGS. 2 and 3.

Although the whole Pain subscale of KOOS in Index Knees demonstrated only a statistical trend ($p<0.09$) of improvement as compared to Control Knees at 12 months, Pain Frequency and Pain Going up or down Stairs showed statistically significant improvement in Index Knees as compared to Control Knees ($p<0.05$). See FIGS. 5 and 6.

Regarding the primary endpoint of the clinical study, which was patella cartilage thickness change at 6 months, there was no statistically significant difference between Index vs. Control Knees. Only 16% of patella cartilage showed any change at all compared with baseline, limiting the de facto sample size for this measure. Nevertheless, the robust clinical benefits demonstrated in favor of TPX-100 are reasonably attributable to cartilage repair, formation, and/or stabilization by the peptide of SEQ ID No. 1.

In a post hoc analysis, an association between positive change in tibiofemoral cartilage thickness and improvement in knee function as measured by KOOS ADL and WOMAC function was observed at 12 months in Index Knees but not in Control Knees (McGuire 2018). Among numerous clinical studies of DMOAD candidates to date, this was the first time that positive cartilage change was demonstrated to be associated with clinical benefits that significantly exceeded those with placebo.

After this publication, further analyses were conducted. These analyses confirmed that tibiofemoral (TF) cartilage thickness increase/stabilization and knee functional improvements were significantly correlated in Index Knees, but not in Control (placebo-exposed) Knees at 12 months after treatment. See Table 1.

TABLE 1

Correlation between Tibiofemoral Cartilage Thickening/Stabilization and Improvement of Knee Function at 6 and 12 Months after Treatment in Index Knees Tibiofemoral Cartilage Thickening/Stabilization vs. Knee Function Measured by KOOS ADL

| | | | Pearson Correlation | | Spearman Correlation | |
|---|---|---|---|---|---|---|
| Month | Variable | N | Correlation | p-value | Correlation | p-value |
| 6 | Lateral TF | 67 | 0.132 | 0.29 | 0.092 | 0.46 |
| | Medial TF | 68 | 0.074 | 0.55 | 0.137 | 0.26 |
| | Entire TF | 67 | 0.122 | 0.33 | 0.110 | 0.38 |
| 12 | Lateral TF | 66 | 0.359 | 0.003 | 0.455 | 0.0001 |
| | Medial TF | 67 | 0.242 | 0.048 | 0.195 | 0.11 |
| | Entire TF | 66 | 0.332 | 0.007 | 0.337 | 0.006 |

With these results, it had been confirmed that the peptide of SEQ ID No. 1 improves clinical benefits and increases/stabilizes TF cartilage thickness in knee OA patients.

Because of the robust findings of multiple clinical benefits associated with treatment with the peptide of SEQ ID No. 1 in a patient population with predominately moderate to severe knee OA, other biological activities in addition to cartilage formation/stabilization may contribute to the peptide's efficacy.

Analysis of Periarticular Bone Area and Shape

To address this question, periarticular bone surface area and three-dimensional (3D) bone shape of Index and Control Knees were measured and compared.

It has been demonstrated that periarticular bone shape is altered in a predictable fashion in normal aging, with acceleration of bone shape changes in association with onset and progression of knee OA. The pattern of periarticular bone shape change is common to all knees that develop OA. Periarticular bone shape flattens and becomes irregular, while bone surface area increases. Such bone shape change begins years earlier than detectable radiographic changes among patients who go on to develop OA (Reichenbach 2008).

The 3D bone shape change can be quantified using active appearance modelling (AAM). AAM enables encoding of the 3D shape and appearance of an object using multiple anchor points ("principal components") on the surface of the object. These principal components describe computationally the specific 3D shape of the object. The use of AAM to represent femur, tibia, and patella shapes has been described in detail by Neogi, et. al. (Neogi 2013).

With this method, periarticular bone area and bone shape changes in OA and non-OA knees of subjects enrolled in the National Institute of Health Osteoarthritis Initiative (OAI) were compared. As described in detail by Bowes, et. al. (Bowes 2015) and Hunter et. al. (Hunter 2016), percentage changes in bone area and changes of bone shape scores for femur, tibia, patella, and trochlear femur (the anterior sub-region of femur which articulates with the patella; this region is also called patellofemoral bone or PF) between OA vs. non-OA knees were compared over a period of four years. Bone area of all regions, regardless of OA status, showed an increase from baseline. Bone shape scores of all regions also increased from baseline. Changes were unidirectional and irreversible per natural history.

OA knees showed a significantly greater rate of bone area increase in all regions as compared to non-OA knees. See FIG. 7. Periarticular bones of OA knees typically showed bone area increases from baseline that were statistically significantly larger compared to non-OA knees as measured over a one-year period (Bowes 2015). Periarticular bones of OA knees also show statistically significantly faster bone shape score increase as compared to non-OA knees.

Results of the clinical trial of TPX-100, where the test articles were administered for only four times in the beginning of the study period (days 0, 7, 14, and 21) without any booster treatments thereafter, demonstrated that periarticular 3D bone shape and bone area of Index (TPX-100-treated) Knees showed slower rate of changes when compared with those in Control Knees by AAM analysis by iMorphics (www.imorphics.com). The MRI images of each knee used in cartilage thickness measurement were used to measure surface area of the periarticular bone in lateral and medial femur, lateral and medial trochlear femur, lateral and medial tibia, as well as lateral and medial patella. Bone shape scores in femur, trochlear femur, tibia, and patella were also measured using the same MRI images.

Periarticular bone area changes in all eight regions were compared between Index vs. Control Knees from the present clinical study.

Control Knees (placebo-treated knees) from the clinical study showed consistent increases in periarticular bone area in all regions similar to those seen in OA knees from the OAI natural history database.

The medial femur of Index Knees demonstrated less periarticular bone area increase as compared to Control Knees at 6 months, with a trend toward statistical significance ($p=0.08$). FIG. 8 shows medial femur bone area change for 6 and 12 months in Index and Control Knees, respectively, after administration of the test articles.

FIG. 9 shows the bone area change of periarticular bones of Index vs. Control Knees in lateral femur, lateral patella, and medial patella, respectively. Although these comparisons did not show statistically significant differences between the treatment arms, it is notable that the bone area change in Index Knees in the first 6 months was nearly zero in all regions.

When comparing 3D bone shape change, Index Knees exhibited a statistically significant decrease in shape change compared to Control Knees. This difference was significant at both 6 and 12 months ($p=0.005$ and $0.007$, respectively). Of note, the mean bone shape change rate for the first 6 months was 0.03 in Index Knees, which was very similar to the mean rate of change of non-OA subjects in the OAI database. See FIG. 10.

Based on analyses of the population participating in the OAI, all knees exhibit a continuous increase in bone areas and changes in 3D shape with aging. These changes are accelerated in knee OA. Slowing, arresting or reversing these bone changes would be disease modifying in OA.

As described in the preceding paragraphs, treatment of mild to severe OA knees with the peptide of SEQ ID No. 1 reduced the rates of 3D bone shape and bone area changes in femur as compared to the placebo-treated knees. This indicates that OA progression was delayed, arrested or, in some cases, even reversed by the peptide of SEQ ID No. 1. The peptide of SEQ ID No. 1 was administered only for one series (4 times on days 0, 7, 14, and 21) in this study. If administration of the peptide of SEQ ID No. 1 is repeated periodically, e.g., every several months, every year or two, etc., pathological 3D bone shape and bone area changes should be reduced or normalized over a longer period.

These data also suggest that the treatment with the peptide of SEQ ID No. 1 delayed, arrested, or even reversed the increase of periarticular bone area, and thereby may delay, arrest, or reverse OA progression and delay or eliminate joint failure associated with natural aging.

It should be noted that these modifications of pathological bone area increase and 3D shape change in periarticular bone by the treatment with the peptide of SEQ ID No. 1 occurred in a relatively short period of time that is 6 and 12 months after treatment.

It was surprising that the decrease in pathological periarticular bone shape changes by the peptide of SEQ ID No. 1 occurred in such a short period of time and that the treatment differences was robust and statistical significance despite a relatively small sample size.

Because clinical benefits in the knees, as measured by KOOS ADL, KOOS Sports and Recreation, and KOOS Knee-Related QOL, were clinically meaningful and statistically significant in favor of Index Knees at 6 months, 12 months, or both; and OA progression, measured by periarticular bone structure change, was delayed, arrested, or reversed in Index Knees as compared to Control Knees, it is believed that the peptide of SEQ ID No. 1 modifies the pathophysiology of OA by modifying periarticular bone structure changes.

To elucidate possible effects of periarticular bone shape improvements by the peptide of SEQ ID No. 1 on the clinical benefits, correlation analyses were carried out using Pearson and Spearman statistical analytic methods.

Among all knee joint regions, the femur is the largest periarticular bone. Structure change in the femur is believed to be highly influential in the pathophysiology and progression of knee OA. The peptide of SEQ ID No. 1 significantly reduced pathological 3D bone shape changes in the femur within 6 months after administration (FIG. 10). Both Pearson and Spearman analyses demonstrated a correlation between the reduction of pathological femur 3D bone shape change and tibiofemoral (TF) cartilage thickening/stabilization in knees treated with the peptide of SEQ ID No. 1 (Index Knees), with robust statistical significance at 12 months. See Table 2. Cartilage thickening/stabilization in the entire TF cartilage, as well as lateral and medial TF and femoral condyle cartilage was significantly correlated with the reduction of 3D bone shape changes in the femur. At 6 months, trends toward significant correlations were observed in the entire TF region as well as in the medial TF region and in the femoral condyle. These results indicate that the significant reduction of pathological 3D femur bone shape change by the peptide of SEQ ID No. 1 manifested relatively early (in the first 6 months), and that the peptide of SEQ ID No. 1 induced TF cartilage thickening/stabilization. Reduction of pathological bone shape change in the femur and TF cartilage increase/stabilization were highly significantly correlated at 12 months.

TABLE 2

Correlation between Reduction of Pathological 3D Bone Shape Change in Femur and Tibiofemoral Cartilage Thickening/Stabilization at 6 and 12 Months after Treatment in Index Knees Reduction of Pathological Femur 3D Bone Shape Change vs. TF Cartilage Thickening/Stabilization

| Month | Tibiofemoral Compartment | N | Pearson Correlation Correlation | Pearson Correlation p-value | Spearman Correlation Correlation | Spearman Correlation p-value |
|---|---|---|---|---|---|---|
| 6 | Entire TF Cartilage | 85 | 0.202 | 0.0633 | 0.189 | 0.0833 |
|   | Lateral TF Cartilage | 84 | 0.109 | 0.3257 | 0.124 | 0.2608 |
|   | Medial TF Cartilage | 85 | 0.206 | 0.0581 | 0.202 | 0.0631 |
|   | Femoral Condyle Cartilage | 85 | 0.187 | 0.0869 | 0.201 | 0.0654 |
| 12 | Entire TF Cartilage | 85 | 0.341 | 0.0014 | 0.380 | 0.0003 |
|   | Lateral TF Cartilage | 84 | 0.227 | 0.0380 | 0.249 | 0.0222 |
|   | Medial TF Cartilage | 85 | 0.359 | 0.0007 | 0.394 | 0.0002 |
|   | Femoral Condyle Cartilage | 85 | 0.346 | 0.0012 | 0.376 | 0.0004 |

The same analyses with bilateral tibiofemoral OA subjects (after isolated patello-femoral OA knees were excluded), despite comprising a more limited sample size, demonstrated a statistically significant correlation at 12 months between the reduction of pathological femur 3D bone shape change and tibiofemoral (TF) cartilage thickening/stabilization in the entire TF region as well as in the medial TF area and in the femoral condyle. See Table 3.

These correlations were identified only in Index Knees and not found in Control Knees in any of the analyses.

TABLE 3

Correlation between Reduction of Pathological 3D Bone Shape Change in Femur and Tibiofemoral Cartilage Thickening/Stabilization at 6 and 12 Months after Treatment in Index Knees of Bilateral Tibiofemoral OA Subjects Reduction of Pathological Femur 3D Bone Shape Change vs. TF Cartilage Thickening/Stabilization

| Month | Tibiofemoral Compartment | N | Pearson Correlation Correlation | Pearson Correlation p-value | Spearman Correlation Correlation | Spearman Correlation p-value |
|---|---|---|---|---|---|---|
| 6 | Entire TF Cartilage | 61 | 0.093 | 0.4739 | 0.111 | 0.3954 |
|   | Lateral TF Cartilage | 60 | 0.047 | 0.7191 | 0.118 | 0.3688 |
|   | Medial TF Cartilage | 61 | 0.084 | 0.5178 | 0.117 | 0.3688 |
|   | Femoral Condyle Cartilage | 61 | 0.057 | 0.6644 | 0.093 | 0.4742 |
| 12 | Entire TF Cartilage | 61 | 0.296 | 0.0205 | 0.366 | 0.0037 |
|   | Lateral TF Cartilage | 60 | 0.173 | 0.1870 | 0.218 | 0.0947 |
|   | Medial TF Cartilage | 61 | 0.329 | 0.0097 | 0.393 | 0.0017 |
|   | Femoral Condyle Cartilage | 61 | 0.282 | 0.0276 | 0.306 | 0.0163 |

The pathological 3D bone shape change in patella was reduced by the peptide of SEQ ID No. 1. At 12 months, both Pearson and Spearman analyses demonstrated a significant correlation between the reduction of pathological patella 3D bone shape change and pain frequency in knees treated with the peptide of SEQ ID No. 1 (Index Knees). See Table 4. The responders to the treatment reduced their pain frequency dramatically during the 12 months follow-up period. See FIG. 11. In the responder group, the baseline pain frequency score was 3 that indicates "daily" pain. At 12 months, the score was improved by approximately 1.5 points, indicating their pain frequency was reduced to "semi-weekly". Use of analgesics by participants in this study decreased by 62.5%.

Further, 3D bone shape change of patella in the pain frequency responder group remained approximately zero through 12 months while that in the non-responder group showed consistent increase. The 3D bone shape change of patella from baseline to 12 months showed highly statistically significant difference between the groups. See FIG. 12.

These combined results indicate that the peptide of SEQ ID No. 1 reduced or possibly reverted pathological 3D bone shape change in patella, thereby dramatically reducing knee pain frequency and use of analgesics.

TABLE 4

Correlation between Reduction of Pathological 3D Bone Shape Change in Patella and Reduction of Pain Frequency at 12 Months after Treatment in Index Knees Patella Periarticular Bone Shape Change vs. Pain

| Month | Pain Scale | n | Pearson Correlation Correlation | Pearson Correlation p-value | Spearman Correlation Correlation | Spearman Correlation p-value |
|---|---|---|---|---|---|---|
| 12 | Pain Frequency | 85 | 0.319 | 0.0029 | 0.373 | 0.0004 |

This correlation between reduction of pathological 3D bone shape change in patella and pain frequency improvement was identified in Index Knees but not in Control Knees.

The pathological 3D bone shape change of the patella has not been characterized as well as that of femur. Whereas the severity of knee pain has been associated most consistently with severity of patellar pathology (Joseph 2016), this invention is the first time that patella 3D bone shape change is specifically proposed as a pathophysiologic mechanism of knee pain in OA. In conventional clinical settings of ad hoc pain treatments, the patient can determine whether or not the pain is reduced shortly after the treatments. In this disease modifying therapy through delaying, arresting, or reversing the pathological 3D bone shape change, pain reduction occurs as a result of the structural effects on the bone, which seems to take a few months based on the present clinical data. Therefore, monitoring of bone shape change after this treatment provides the patients and caregivers with useful information regarding prognosis such as whether or not the patient's current knee pain could be reduced or prevented from worsening and/or whether or not the repeated treatment could benefit further. Treatment and prevention of knee pain by reducing pathological patella bone shape change is one of the most important components of this invention.

In summary, administration of the peptide of SEQ ID No. 1 in knee OA patients induces significant slowing or even reversion of pathological periarticular 3D bone shape changes in multiple knee joint compartments, resulting in desired clinical benefits including improved function and reduction in frequency of knee pain. The peptide of SEQ ID No. 1 positively affects both periarticular bone and cartilage structure over the same time course; therefore, pathological changes in both components of the knee joint can be treated by a therapeutic composition comprising the peptide of SEQ ID No. 1 as a single pharmaceutical ingredient. Depending on dosing regimen, the peptide of SEQ ID No. 1 not only treats OA but also delays, arrests or reverses pathological changes of joint aging, indicating that the peptide can be used prophylactically to prevent or delay the onset of OA. Because the basic mechanisms of OA are common to many joints, the therapeutic or prophylactic use of the peptide of SEQ ID No. 1 for OA is not limited to OA of the knee but may include hip, ankle, elbow, shoulder, neck, spine, wrist and finger joints. Also, this method can be used to repair, rebuild, or stabilize a joint affected by other arthritis such as rheumatoid arthritis after their disease specific causes such as autoimmunity and inflammation have been managed.

Novel Method of Treating Osteoarthritis

Based on the clinical study results summarized above, a novel method of treating osteoarthritis (OA) has been established.

The method comprises any therapeutic intervention that can delay, arrest, or reverse pathological periarticular bone shape change thereby treating OA. While the pathological nature of periarticular bone shape change for onset and progression of knee OA are supported by data from the natural history studies of OA patients participating in the OAI, the clinical study results described herein have for the first time demonstrated that such naturally irreversible periarticular bone shape change associated with OA can be delayed, arrested, and even reversed. Most importantly, delay, arrest or reversal of periarticular bone shape change correlates with clinically meaningful patient benefits, including function and pain of the affected joint. The present invention confirms in a controlled human clinical trial that slowing pathological periarticular bone shape change is possible and correlates with improvement in critical symptoms of knee OA.

An important component of the method comprises injecting a patient afflicted with OA with a formulation of peptide of SEQ ID No. 1 in a therapeutically effective amount, thereby reducing the rate of bone area and bone shape change in affected joints. Because periarticular bones in osteoarthritic joints show faster increases in bone area and 3D shape changes as compared to non-arthritic joints, reducing the rate of these changes means delaying, arresting or even reversing the progression of OA. These periarticular bone structure changes have been shown to begin before measurable cartilage loss and continue throughout the progression of the disease, this new method can be used across the spectrum of OA, from onset through severe disease.

In addition to the peptide of SEQ ID No. 1, its orthologue peptides derived from other species than human, including but not limited to primates, canine, bovine, and murine are expected to have a similar activity on the periarticular bone structure change of a joint in human and other species, and therefore are within the scope of this invention. The examples are the peptides of SEQ ID No. 2-5.

Analogue peptides of the peptide of SEQ ID No. 1, its orthologues, which are believed to have similar biological activities to the peptide of SEQ ID No. 1, including those sharing a common amino acid sequence shown as SEQ ID No. 6 are within the scope of this invention as well.

Further, since the knee joint is known to undergo periarticular bone area increase and 3D bone shape change as part of the aging process, this method, by reducing the rate of pathological periarticular bone area and shape changes, includes preventing, delaying or arresting an otherwise inevitable process that increases the risk of OA.

This new method works particularly well in knee OA as demonstrated in the EXAMPLES.

One of important components of this invention is a new method to reduce knee pain frequency in knee OA by delaying, arresting, or reversing 3D bone shape change in patella.

A pharmaceutical composition containing the peptide of SEQ ID No. 1, which treats OA by delaying, arresting, or reversing pathological structural change of periarticular bone is within the scope of this invention.

Although this invention is based on the data from clinical trials in knee OA patients, it is applicable to OA in other joints such as hip, ankle, elbow, shoulder, neck, spine, wrist, fingers, and so forth, because similar pathological change in periarticular bone structure should occur in such other joints as well.

Because periarticular bones are often damaged in many joint diseases and disorders, and since the peptide of SEQ ID No. 1 can delay, arrest, or reverse pathological periarticular bone structure changes, this new method can be used to treat joint conditions other than OA, including, but not limited to, rheumatoid arthritis and trauma-induced arthritis.

EXAMPLES

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A Randomized Double-blind Placebo Control Study of TPX-100 in the Patients with Osteoarthritis of the Knees Clinical Study Methodology
Outline of the Study A multicenter, randomized double-blind, placebo-controlled study was designed to investigate the safety, tolerability, pharmacokinetics, and efficacy of TPX-100 administered in four weekly doses in subjects with bilateral patello-femoral knee osteoarthritis. The study was conducted under an open IND (investigational new drug application) at CDER (Center for Drug Evaluation and Research) of the U.S. FDA (The United States Food and Drug Administration) in compliance with GCP (Good Clinical Practice) and ICH (International Conference on Harmonization of Technical Requirements for Registration of Pharmaceuticals for Human Use) guidelines. Eighteen (18) orthopedic, rheumatologic and family practice centers in the U.S. participated in the study.

The study was divided into Part A and Part B. The Part A was designed to evaluate safety of intra-articular (I.A.) administration of TPX-100 at different dosing levels (20, 50, 100, or 200 mg per injection in sequential cohorts) in the subjects with osteoarthritis of the knees and to select a dose for Part B. Part B was to evaluate safety and efficacy of the selected dose of TPX-100.

Subjects in Part A were enrolled in sequential cohorts and randomized to receive 20, 50, 100 or 200 mg of TPX-100 in one knee (Index Knee) and identical placebo in the contralateral (Control) knee. Subjects, sites and sponsor and central MRI readers were blinded as to treatment assignment. A Safety Review Committee (SRC) evaluated safety in each dosing cohort. The SRC assessed safety and determined whether the next higher dosing regimen could be enrolled. All dosing cohorts in Part A were completed and analyzed with regard to safety prior to dose selection and initiation of Part B.

Part A included four (4) intra-articular (I.A.) injections, one per week, in sequential dosing cohorts of 20, 50, 100 and 200 mg TPX-100 versus placebo. Six (6) subjects were enrolled in 20, 50, and 100 mg cohorts, respectively, and nine (9) subjects were enrolled in the 200 mg cohort.

The 200 mg dose was selected for Part B based on safety review and the approval of the SRC. There were no dose-limiting toxicities for this dose or the 3 lower doses investigated in Part A. Eighty-seven (87) subjects were registered in Part B (200 mg dose). Per the Statistical Analysis Plan, these subjects were combined with the nine subjects in the 200 mg cohort of Part A for the efficacy analysis. In total, data from 93 subjects was analyzed for drug efficacy, each of whom received 4 once-weekly injections of TPX-100, 200 mg/dose, in the Index knee and identical placebo in the contralateral knee, as randomly assigned.

In both Part A and Part B, subjects received 4, once-weekly doses of active drug in the knee randomized to active drug in the Index knee and placebo in the contralateral (Control) knee, delivered by the intra-articular route. No other doses of drug or placebo were administered. All subjects visited their respective clinical sites at 3, 6, and 12 months after the first dosing for their safety and efficacy assessments.

Screening of the Subjects

After informed consent was obtained, subjects underwent a clinical and laboratory screening evaluation at which their preliminary eligibility for the study was evaluated. Screening included the following procedures:

Medical history including medication history
Focused physical examination
Vital signs including resting blood pressure, pulse, respiratory rate, and temperature
Weight, height, and BMI
X-ray of the knees (if not obtained within 3 months of screening)
Laboratory evaluations including hematology, coagulation profile, comprehensive metabolic panel, etc.
Recording of concomitant medications Subjects who met all clinical and laboratory eligibility criteria underwent standardized bilateral knee MRIs.

Inclusion and Exclusion Criteria

Inclusion and exclusion criteria for screening of the subjects for either Part A or Part B were as follows:

Inclusion Criteria
1. Age≥25 and ≤75
2. Patello-femoral osteoarthritis of both knees of mild to moderate severity with intact meniscus and ligamentous stability (cruciate and collateral ligaments)
   Clinically, as determined by screening questionnaire, judgment of the Principal Investigator (may be supporting by imaging studies of knees); confirmed by centrally read screening MRI of both knees, of ICRS Grade 1-3, or Grade 4 with only focal defects, no defect greater than 1cm.
   Meniscus intact (MRI degenerative signal up to and including grade II acceptable)
   Cruciate and collateral ligament stability as defined by clinical examination
3. Able to read, understand, sign and date the subject informed consent
4. Willingness to use only acetaminophen as the primary analgesic (pain-relieving) study medication. The maximum dose of acetaminophen must not exceed 4 grams/day (4000 mg) per day.
5. Willingness to use only hydrocodone/acetaminophen or hydrocodone alone for breakthrough pain during the injection period (through study day 30).
6. Willingness not to use non-steroidal anti-inflammatory drugs (NSAIDS) such as aspirin, ibuprofen or naproxen for the first 30 days of the study.
7. Female subjects of child bearing potential who are sexually active (non-abstinent) must agree to and comply with using 2 highly effective methods of birth control (oral contraceptive, implant, injectable or indwelling intrauterine device, condom with spermicide, or sexual abstinence) while participating in the study.

Exclusion Criteria
1. Contraindication to MRI, including: metallic fragments, clips or devices in the brain, eye, or spinal canal; implanted devices that are magnetically programmed; weight>300 lbs.; moderate or severe claustrophobia; previous intolerance of MRI procedure
2. ICRS greater than Grade 3, excepting Grade 4 with focal defects no greater than 1cm as confirmed by centrally-read screening MRI
3. MRI evidence of inflammatory or hypertrophic synovitis, or significant chondral calcification
4. Prior surgery in the knees, excluding procedures for debridement only
5. Knee joint replacement or any other knee surgery planned in the next 12 months
6. History of rheumatoid arthritis, psoriatic arthritis, or any other autoimmune or infectious cause for arthritis
7. Knee effusion>2+ on the following clinical scale:
Zero=No wave produced on downstroke
Trace=Small wave on medial side with downstroke
1+=Larger bulge on medial side with downstroke
2+=Effusion spontaneously returns to medial side after upstroke (no downstroke necessary)
3+= So much fluid that it is not possible to move the effusion out of the medial aspect of the knee
8. Last viscosupplementation (e.g. Synvisc® or similar hyaluronic acid product) injected into either knee<3 months before screening
9. Last intra-articular knee injection of corticosteroids<2 months before screening
10. Use of any steroids (except inhaled corticosteroids for respiratory problems) during the previous month before screening
11. Known hypersensitivity to TPX-100
12. Known hypersensitivity to acetaminophen or hydrocodone
13. History of arthroscopy in either knee in the last 3 months before screening
14. History of septic arthritis, gout or pseudo-gout, of either knee in previous year before screening
15. Clinical signs of acute meniscal tear (e.g. locking or new acute mechanical symptoms consistent with meniscal tear)
16. Patellar chondrocalcinosis on X-Ray
17. Skin problem, rash or hypersensitivity, affecting either knee at the injection site
18. Bleeding problem, platelet or coagulation deficiency contraindicating intra-articular injection
19. Active systemic infection 20. Current treatment or treatment within the previous 2 years prior to the Screening Visit for any malignancy except basal cell or squamous cell carcinoma of the skin, unless specific written permission is provided by the Sponsor's medical monitor
21. Women of childbearing potential who are pregnant, nursing, or planning to become pregnant, and those who do not agree to remain on an acceptable method of birth control throughout the entire study period
22. Participation in other clinical osteoarthritis drug studies, with the exception of analgesic studies, within one year prior to screening
23. Currently taking Paclitaxel (mitotic inhibitor), and or Natalizumab (anti-integrin).
24. History of significant liver disease or consumption of more than 3 alcoholic drinks a day. (Definition of one alcoholic drink: 12-ounces of beer, 8-ounces of malt liquor, 5-ounces of wine, 1.5-ounces or a "shot" of 80-proof distilled spirits or liquor such as gin, rum, vodka, or whiskey).

Randomization

If all clinical inclusion and exclusion criteria were met, MRIs of both knees were obtained and evaluated by a central reader to determine the ICRS grade (gICRS) of each knee as the final screening criterion. If the cartilage of patello-femoral compartment in both knees fell within ICRS grades 1-3, or 4 with only small focal defects no greater than 1 cm, the subject was registered. The randomization center randomized each subject to either "Right knee active" or "Left knee active". The active knee was to receive TPX-100 and the contralateral knee was to receive identical placebo.

For enrolled subjects, there was within-subject randomization, such that one knee received active drug injections, and the contralateral knee received identical placebo injections. As two knees within a person form a matched set, the effects of individual-level confounders (e.g. level of activity, genetic and epigenetic factors, pain threshold) are eliminated, increasing the power of the study to detect a treatment effect if one is present.

Any subject who was randomized in Part A was excluded from enrollment in Part B.

Dosing

On the first dosing day, the randomized subjects were assessed by physical examinations and vital signs. Further, they completed the Knee injury and Osteoarthritis Outcome Score (KOOS), which includes the Western Ontario and McMaster Universities Osteoarthritis Index (WOMAC). The KOOS questionnaire assesses knee-specific activities of daily living, sports and recreation, knee-related quality of life, other symptoms such as stiffness, and knee pain. The KOOS has been used extensively in longitudinal studies of knee osteoarthritis. After assessments were completed, subjects received one intra-articular injection in each knee, with each injection prepared from the vial(s) marked for that knee. One knee received TPX-100, and the contralateral knee received placebo with subject, site, and sponsor blinded to treatment assignment. Subjects were monitored for adverse events during the injections and for a few hours after the injections. Vital signs were also monitored after the injections.

On the 7th, 14th, and 21st days after the first dosing, subjects received the second, third, and fourth (last) dosing of the same study materials, respectively. Safety and adverse event assessments were obtained as on the first dosing day.

Post-Treatment Follow-Up

Subjects returned to their respective study sites at 3, 6 and 12 months after the first dosing day for follow-up evaluations. In addition, the study sites monitored the subject's condition through telephone contact 9 months after the first dosing day. During the 3, 6, and 12 months post-treatment, subjects were evaluated on site with physical examinations, vital signs, serum chemistries, as well as completing patient-reported outcomes including the KOOS. Adverse events and concomitant medications were recorded. MRIs of both knees were obtained during the 6 and 12-month visits.

Efficacy Analyses

All KOOS subscale scores, WOMAC Total score and subscale scores, MRI-based patello-femoral and tibiofemoral cartilage thickness, and MRI-based periarticular bone area and 3D bone shape were analyzed.

MRI images were provided to central readers cartilage and periarticular bone measures. Central readers were blind as to treatment assignment.

Bone area and 3D shape of periarticular bone were analyzed using AAM software developed by (www.imorphics.com www.imorphics.com) specifically for assessing these parameters in the osteoarthritic knee.

Statistical analyses were carried out using a two-sided paired t-test at the 5% level of significance. The outcome variables were the differences of the change of the score of each subscale of KOOS, change of cartilage thickness, periarticular bone area, and 3D bone shape score ("B Score") change from baseline to 6 and 12 months in the treated knee ("Index Knee") compared with the placebo-exposed knee ("Control Knee").

Regarding possible correlations between any two selected parameters (e.g., knee function vs. cartilage thickness), Pearson and Spearman correlation analyses were employed to test them.

Results

Ninety-three (93) subjects who received 200 mg per dose of TPX-100 in one knee and placebo in contralateral knee and who had at least one follow-up MRI were included in the efficacy analysis per the Statistical Analysis Plan.

Approximately 47% of all knees had gICRS 4 (the most severe) knee OA, all of which were in the tibiofemoral (TF) compartment. Another approximately 40% had gICRS 3 (the second most severe) knee OA in patello-femoral (PF) and/or TF compartments, and the remaining approximately 20% had gICRS 2 (moderate) PF and/or TF in one or both knees. There were no subjects with gICRS 1 (mild) knee OA. The mean body mass index (BMI) of all subjects exceeded 30, which is in the obese range and consistent with the average BMI for the OA population in the U.S. The average age of the subjects was 58.1, and 58% of the subjects were female, also consistent with the demographics for the U.S. OA population. Most subjects had severe OA in one or both knees.

The TPX-100 treatments were safe and well tolerated. There were no severe adverse events that were related to TPX-100 treatment. Treatment-related adverse events were mild or moderate, transient, and common in many subjects at baseline.

Several patient-reported outcomes (PROs), including a majority of KOOS subscales, demonstrated clinically meaningful and statistically significant improvements in the Index (TPX-100 treated) knees as compared to the Control (placebo-exposed) knees.

The KOOS ADL (Function in Activities of Daily Living) subscale consists of 17 questions pertaining to various daily activities critical to everyday knee function. Results of the KOOS ADL domain demonstrated clinically meaningful and statistically significant ($p<0.05$) improvements over baseline in Index Knees as compared to Control Knees at both 6 and 12-month time points. See FIG. 1. The WOMAC Function subscale, which consists of the same questions as KOOS ADL, unsurprisingly also showed the same robust improvement in Index Knees as compared to Control Knees.

The KOOS Sports and Recreation subscale consists of five questions pertaining to sporting activities such as jumping, running, and squatting. The KOOS Sports and Recreation showed clinically meaningful and statistically significant improvement in Index Knees as compared to Control Knees at 6 months. See FIG. 2.

The KOOS Knee-related Quality of Life (QOL) subscale consists of four questions including the subjects' general difficulty with their knee and awareness of problems with confidence regarding each of their knees. The KOOS Knee-related QOL exhibited clinically meaningful and statistically significant improvement in Index Knees as compared to Control Knees at 12 months. See FIG. 3.

The KOOS Pain subscale consists of 9 questions regarding 1) frequency of pain and 2) amount of pain in performing different activities. See FIG. 4. The KOOS Pain subscale demonstrated clinically meaningful improvement in Index Knees as compared to Control Knees at 12 months, with a trend towards statistical significance ($p<0.09$). The WOMAC Pain domain, which consists of questions 6-9 in FIG. 4, demonstrated a clinically meaningful improvement in Index Knees at 12 months compared with Control knees, although the difference did not reach statistical significance.

One of the questions making up the KOOS Pain (and WOMAC Pain) subscale queries "Pain going up or down stairs". Pain during this common activity is one of the most common complaints made by patients with knee OA and was significantly improved ($p<0.05$) in Index Knees as compared to Control Knees at 12 months. See FIG. 5.

One question in the KOOS Pain subscale (question 1) asks, "How often do you experience RIGHT/LEFT knee pain?" This is the only question pertaining to frequency of pain. This question is unique to the KOOS Pain subscale and is not included in the WOMAC Pain domain Pain Frequency was significantly reduced ($p<0.05$) in Index Knees as compared to Control Knees at 12 months. See FIG. 6.

Patello-femoral cartilage thickness change from baseline at 6 months, as measured by MRI, was the primary efficacy outcome measure. There was no measurable difference between Index and Control Knees at either 6 or 12-months. The vast majority (84%) of knees had less than minimum detectable change in cartilage thickness change in the patello-femoral compartment over the 12-month study period. With only 16% of knees demonstrating measurable change in cartilage, whether increased or decreased, the effective sample size was markedly limited, and the power to detect a treatment difference was correspondingly low.

Similarly, overall tibiofemoral cartilage thickness change from baseline was not measurably different between Index and Control Knees at 6 or 12-month time point. However, among knees with improvement in function, as measured by KOOS ADL and WOMAC Function domains, tibiofemoral cartilage thickness increase or stabilization correlated significantly with knee function improvement at 12 months in Index Knees. This correlation was not found in Control Knees. See Table 1.

Change in periarticular bone area and 3D bone shape as measured by MRI was also compared between Index and Control Knee groups. It should be noted that there were eight subjects whose MRI images were of insufficient quality and were excluded from bone area and shape analyses. Therefore, each evaluable treatment arm consisted of 85 knees.

In the medial femur, Index Knees demonstrated less pathological bone area increase as compared to Control Knee at 6 months, with a trend toward statistical significance ($p=0.08$). See FIG. 8.

In the lateral femur and lateral and medial patella, pathological bone area increase in the first 6 months was nearly zero in Index Knees in the first 6 months, with slower increase at 12 months compared with Control Knees. See FIG. 9.

These data indicate that treatment of knee OA with the peptide of SEQ ID No. 1 delays, arrests, or even reverses periarticular bone area increase in the knees associated with onset and progression of OA.

Three-dimensional (3D) periarticular bone shape change of femur as quantified by the bone shape (B) score showed a statistically significant ($p<0.05$) difference in favor of Index Knees as compared to Control Knees at both 6 and 12 months. See FIG. 10.

Although there was no statistically significant difference, 3D periarticular bone shape changes in tibia and patella also demonstrated slower changes in Index Knees as compared to Control Knees. These data also demonstrate treatment of knee OA with the peptide of SEQ ID No. 1 delays, arrests, or reverses periarticular bone structure changes that are pathological to progression of knee OA.

As shown in Table 1, tibiofemoral cartilage thickening/stabilization significantly correlated with KOOS ADL/WOMAC Function improvement in Index Knees, but not in Control Knees. Further analysis demonstrated that less change in 3D periarticular femur bone shape significantly correlated with tibiofemoral cartilage thickening/stabilization in Index knees but not in Control knees. See Tables 2 and 3. These results suggest that treatment of knee OA patients with the Peptide of SEQ ID No. 1 slowed pathological periarticular bone shape change in femur, increased/stabilized tibiofemoral cartilage thickness, and improved knee function simultaneously.

In the literature on symptomatic knee OA, patello-femoral pathology has been most clearly associated with pain complaints. In Index Knees, but not in Control Knees, slower patella bone shape change significantly correlated with a reduction in pain frequency. See Table 4.

Further, responders to TPX-100 demonstrated robust improvements in pain frequency, which were, on average, decreased from daily pain at baseline to semi-monthly pain at 12 months. See FIG. 11. The robust improvement of pain frequency was also associated with eventually no change in the 3D bone shape in patella. See FIG. 12. Notably, overall analgesic use was reduced by 62.5% over the 12-month study period.

Based on these clinical data in mild to severe knee OA patients, the peptide of SEQ ID No. 1 significantly reduced, arrested, or even reversed pathological periarticular bone structure change in multiple compartments in the knee joint and provided critical benefits to patients including improvements in knee function and pain.

Example 2

A Randomized Double-Blind Placebo Control Study of TPX-100 in the Patients with Osteoarthritis of the Knees—Data Analysis with Stricter Qualification Standard Applied to the MRI Image Quality Objectives After the data analyses in EXAMPLE 1, a few more MRI images were questioned with regard to their technical quality to enable assessment of periarticular bone shape change over time. In order to assure the quality of the overall analysis results, a stricter qualification standard was applied to the MRI images used in EXAMPLE 1, and requalification was performed. Seventy-nine (79) subjects were requalified. The MRI knee images of these subjects were re-analyzed for their periarticular bone shape changes, as well as their correlations with the changes of tibiofemoral cartilage thickness and pain, respectively, in the same manner as described in EXAMPLE 1.

Results

The requalified 79 subjects were included in the efficacy analysis per the Statistical Analysis Plan.

Approximately 34% of all knees had gICRS 4 (the most severe) knee OA, all of which were in the tibiofemoral (TF) compartment. Another approximately 44% had gICRS 3 knee OA in patello-femoral (PF) and/or TF compartments, and the remaining approximately 22% had gICRS 2 (moderate) PF and/or TF in one or both knees. The patient demographics were very similar to those of EXAMPLE 1; mean body mass index (BMI) was 30.9, the average age was 58.1, and 62% of the subjects were female.

All knee function and quality of life (QOL)-related patient-reported outcomes (PROs) of Index (TPX-100-treated) knees demonstrated clinically meaningful and statistically significant ($p<0.05$) improvements as compared to Control (placebo-exposed) knees at 6 or 12 month, or both time points: KOOS ADL (Function in Activities of Daily Living), WOMAC Function, and KOOS Knee-related QOL.

The KOOS Pain subscale also demonstrated similar results to those in EXAMPLE 1: clinically meaningful improvement in Index Knees with a trend towards statistical significance ($p<0.09$) as compared to Control Knees at 12 months.

Among nine questions making up the KOOS Pain subscale queries, pain frequency, pain bending knee fully, and pain going up or down stairs were significantly improved ($p<0.05$) in Index Knees as compared to Control Knees at 12 months.

With regard to the 3D periarticular bone shape change as quantified by the bone shape score, Index Knees showed statistically significant ($p<0.05$) delay of femur bone shape change as compared to Control Knees at both 6 and 12 months. See FIG. 13.

As shown in Table 5, less change in 3D periarticular femur bone shape significantly correlated with tibiofemoral cartilage thickening/stabilization in Index knees but not in Control knees.

TABLE 5

Correlation between Reduction of Pathological 3D Bone Shape Change in Femur and Tibiofemoral Cartilage Thickening/Stabilization at 6 and 12 Months after Treatment in Index Knees Femur Bone Shape Change vs. Tibiofemoral Cartilage Thickness Increase/Stabilization

| Month | Tibiofemoral Compartment | n | Pearson Correlation | | Spearman Correlation | |
|---|---|---|---|---|---|---|
| | | | Correlation | p-value | Correlation | p-value |
| 6 | Entire TF Cartilage | 78 | 0.193 | 0.0900 | 0.162 | 0.1552 |
| | Lateral TF Cartilage | 77 | 0.089 | 0.4419 | 0.109 | 0.3453 |
| | Medial TF Cartilage | 78 | 0.212 | 0.0618 | 0.196 | 0.0857 |
| | Femoral Condyle Cartilage | 78 | 0.206 | 0.0705 | 0.215 | 0.0584 |
| 12 | Entire TF Cartilage | 78 | 0.296 | 0.0085 | 0.340 | 0.0023 |
| | Lateral TF Cartilage | 77 | 0.181 | 0.1155 | 0.188 | 0.1010 |
| | Medial TF Cartilage | 78 | 0.320 | 0.0043 | 0.371 | 0.0008 |
| | Femoral Condyle Cartilage | 78 | 0.302 | 0.0071 | 0.341 | 0.0022 |

In Index Knees, but not in Control Knees, slower patella bone shape change significantly correlated with a reduction in pain frequency. See Table 6.

TABLE 6

Correlation between Reduction of Pathological 3D Bone Shape Change in Patella and Reduction of Pain Frequency at 12 Months after Treatment in Index Knees Patella Periarticular Bone Shape Change vs. Pain

| Month | Pain Scale | N | Pearson Correlation | | Spearman Correlation | |
|---|---|---|---|---|---|---|
| | | | Correlation | p-value | Correlation | p-value |
| 12 | Pain Frequency | 79 | 0.347 | 0.0017 | 0.411 | 0.0002 |

Further, responders to TPX-100 demonstrated robust improvements in pain frequency, which were, on average, decreased from daily pain at baseline to semi-monthly pain at 12 months. See FIG. 14. The robust improvement of pain frequency was also associated with eventually no change in the 3D bone shape in patella. See FIG. 15.

In this EXAMPLE 2, very similar results to those in EXAMPLE 1 were obtained with the data set under stricter control on the quality of the MRI images. Based on these data, the peptide of SEQ ID No. 1 significantly reduced, arrested, or even reversed pathological periarticular bone structure change in multiple compartments in the knee joint and provided critical benefits to patients including improvements in knee function and pain.

REFERENCES

Bowes M A, Vincent G R, Wolstenholme C B, Conaghan P G. A novel method for bone area measurement provides new insights into osteoarthritis and its progression. *Ann Rheum Dis* 2015; 74:519-525.

Buckwalter J A. Articular cartilage injuries. *Clin Orthop Relat Res* 2002; 21-37

Chevalier X, et al. Single, intra-articular treatment with 6 cc hylan G-F 20 in subjects with symptomatic primary osteoarthritis of the knee: a randomized, multi-centre, double-blind, placebo-controlled trial. *Ann Rheum Dis* 2010; 69: 113-119.

Cohen M D. Hyaluronic acid treatment (viscosupplementation) for OA of the knee. *Bull Rheum Dis*. 1998; 47; 4-7.

Davies A P, Vince A S, Shepstone L, Donell S T, Glasgow M M., The Radiographic Prevalence of Patellofemoral Osteoarthritis. *Clinical Orthopaedics and Related Research* 2002; 402:206-212

Dube B, Bowes M A, Barr A J, Hensor E M, Kingsbury S R, Conaghan P G., The relationship between two different measures of osteoarthritis bone pathology, bone marrow lesions and 3D bone shape: data from the osteoarthritis initiative. *Osteoarthritis and Cartilage* 2018; 26:1333-1337

FDA (U.S. Department of Health and Human Services, Food and Drug Administration). Osteoarthritis: Structural Endpoints for the Development of Drugs, Devices, and Biological Products for Treatment Guidance for Industry. *DRAFT GUIDANCE* August 2018

Felson D T, Hannan M T, Naimark A, Berkeley J, Gordon g, Wilson P W, et. al. Occupational Physical Demands, knee bending, and knee osteoarthritis: results from the Framingham Study. *J Rheumatol.* 1991; 18:1587-92.

Guermazi A, Kalsi G, Niu J, Crema M D, Copeland R O, Orlando A, Noh M I, Roemer F W. Structural effects of intra-articular TGF-β1 in moderate to advanced knee osteoarthritis: MRI-based assessment in a randomized controlled trial. *BMC Musculoskeletal Disord* 2017; 18:461

Haj-Mirzaian A, Guermazi A, Roemer F W, Bowes M A, Conaghan P G, Demehri S. Bisphosphonates intake and its association with changes of periarticular bone area and three-dimensional shape: data from the osteoarthritis Initiative (OAI). *Osteoarthritis and Cartilage* 2018; 26:564-568

Hardcastle S A, Gregson C L, Deere K C Smith G D, Dieppe P, Tobias J H. High bone mass is associate with an increased prevalence of joint replacement: a case-control study. *Rheumatology* 2013; 52:1042-1051

Hayashibara T, Hiraga T, Yi B, Nomizu M, Kumagai Y, Nishimura R, Yoneda T. A synthetic peptide fragment of human MEPE stimulates new bone formation in vitro and in vivo. *JBMR* 2004; 19:455

Hellio le Graverand M P, Clemmer R S, Redifer P, Brunell R M, Hayes C W, Brandt K D, Abramson S B, Manning P T, Miller C G, Vignon E. A 2-year randomized, double-blind, placebo-controlled, multicenter study of oral selective iNOS inhibitor, cindunistat (SD-6010), in patients with symptomatic osteoarthritis of the knee. *Ann Rheum Dis* 2013; 72:187-195

Hochberg M C, Guermazi A, Guehring H, Aydemir A, Wax S, Fleuranceau-Morel P, Bihlet A R, Byrjalsen I, Andersen J R, Eckstein F. Efficacy and safety of intra-articular Sprifermin in symptomatic radiographic knee osteoarthritis: results of the 2-year primary analysis from a 5-year randomized, placebo-controlled, Phase 2 study. *Arthritis Rheumatol* 2017; 69 (suppl 10):1 L Hochberg M C, Guermazi A, Guehring H, Aydemir A, Wax S, Fleuranceau-Morel P, Bihlet A R, Byrjalsen I, Andersen J R, Eckstein F. Efficacy and safety of intra-articular Sprifermin in symptomatic radiographic knee osteoarthritis: pre-specified analysis of 3-year data from a 5-year randomized, placebo-controlled, Phase II study. *Osteoarthritis and Cartilage* 2018; 26:S32

Hunter D, Nevitt M, Lynch J, Kraus V B, Katz J N, Collins J E, Bowes M, Guermazi A, Roemer F W, Losing E. Longitudinal validation of periarticular bone area and 3D shape as biomarkers for knee OA progression? Data from the FNIH OA Biomarkers Consortium. *Ann Rheum Dis* 2016; 75:1607-1614.

Joseph G B, Hou S W, Nardo L, Heilmeier U, Nevitt M C, McCulloch C E, Link T M. MRI findings associated with development of incident knee pain over 48 months: data from the osteoarthritis initiative. *Skeletal Radiol.* 2016; 45(5):653-660

Karsdal M A, Byrjalsen I, Alexandersen P, Bihlet A, Andersen J R, Riis B J, Bay-Jensen A C, Christiansen C. Treatment of symptomatic knee osteoarthritis with oral salmon calcitonin: results from two phase 3 trials. *Osteoarthritis Cartilage* 2015; 23(4):532

Krsezki P, Buckland-Wright C, Balint G, Cline G A, Stoner K, Lyon R, Beary J, Aronstein W S, Spector T D. *Arthritis Res Ther* 2007; 9 (5):R109

Laslett L L, Dore D A, Quinn S J, Boon P, Ryan E, Winzenberg T M, Jones G. Zolendronic acid reduces knee pain and bone marrow lesions over 1 year: a randomized controlled trial. *Ann Rheum Dis* 2012; 71:1322-8

Lazarov M, Shih M S, Gerome C, Blacher R, Kumagai Y, Rosen D M. AC-100, a fragment of MEPE, promotes fracture healing in a rat model. *ASBMR* 2004

Lazarov M, Fellmann J, Rosen D M, DenBesten P K, Pameijer C H. AC-100, novel biological approach to promoting dentin formation in humans. *AADR* 2006

McAlindon T E, LaValley M P, Harvey W F, Price L L, Driban J B, Zhang M, Ward R J. Effect of Intra-articular triamcinolone vs saline on knee cartilage volume and pain in patients with knee osteoarthritis—a randomized clinical trial. *JAMA* 2017; 317(19): 1967-1975.doi: 10.1001/jama.2017.5283

McGuire D, Lane N, Segal N, Metyas S, Barthel H R, Miller M, Rosen D, Kumagai Y. Significant, sustained improvement in knee function after intra-articular TPX-100: A double-blind, randomized, multi-center, placebo-controlled Phase 2 trial. *Arthritis Rheumatol* 2017; 69 (suppl 10):13 L.

McGuire D, Segal N, Metyas S, Barthel H R, Miller M, Rosen D, Kumagai Y. Intra-articular TPX-100 in knee osteoarthritis: Robust functional response at 6 and 12 months is associated with increased tibiofemoral cartilage thickness. *Arthritis Rhematol* 2018; 70 (suppl10):L16

Neogi T, Bowes M, Niu J, De Souza K, Vincent G, Goggins J, Zhang Y, Felson D T. MRI-based three-dimensional bone shape of the knee predicts onset of knee osteoarthritis: Data from the Osteoarthritis Initiative. *Arthritis Rheum.* 2013; 65(8):2048-2058

Nevitt, M, Zhang Y, Javaid, M K, Neogi T, Curtis J R, Niu J, McCulloch C E, Segal N A, Felson D T. High systemic bone mineral density increases the risk of incident knee OA and joint space narrowing, but not radiographic progression of existing knee OA: The MOST study. *Ann Rheum Dis.* 2010; 69(1):163-168

Niemeyer, M D, et al.: Characteristic Complications After Autologous Chondrocyte Implantation for Cartilage Defects of the Knee Joint. *Am J Sports Med* 2008; 36:2091-2099

Reginster J Y, Badurski J, Bellamy N, Bensen W, Chapurlat R, Chevalier X, Christiansen C, Genant H, Navarro F, Nasonov e, Sambrook P N, Spector T D, Cooper C. Efficacy and safety of strontium ranelate in the treatment of knee osteoarthritis: results of a double-blind, randomized placebo-controlled trial. *Ann Rheum Dis* 2013; 72:179-186.

Reichenbach S, Guermazi A, Niu J, Neogi T, Hunter D J, Roemer F W, McLennan C E, Hernandez-Molina G, Felson D T. Prevalence of Bone Attrition on Knee Radiographs and MRI in a Community-based Cohort. *Osteoarthritis Cartilage* 2008; 16(9): 1005-1010

Sandmark H. Hogstedt C, Vingord E. Primary osteoarthritis of the knee in men and women as a result of lifelong physical load from work. *Scand J Work Environ Health* 2000; 26:20-5.

Six N, Septier D., Chaussain-Miller C, Blacher R, DenBesten P, Goldberg M. Dentonin, a MEPE Fragment, Initiates Pulp-healing Response to Injury. *J Dent Res* 2007; 86(8): 780-785

Woolf A D, Pfleger B, Burden of major musculoskeletal conditions. *Bulletin of the World Health Organization* 2003; 81 (9): 646-656.

Zaslav K, et al. A prospective study of autologous chondrocyte implantation in subjects with failed prior treatment for articular cartilage defect of the knee: Results of the Study of the Treatment of Articular Repair (STAR) clinical trial. *Am J Sports Med.* 2009; 37:42-55.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of delaying or reducing pathological bone shape change of a subchondral bone in a joint of a patient having osteoarthritis, comprising:
   (i) obtaining a first image of the subchondral bone using magnetic resonance imaging (MRI), and measuring three-dimensional (3D) bone shape of the subchondral bone from the first MRI image, thereby diagnosing pathological bone shape change of the subchondral bone and osteoarthritis progression in the joint;
   (ii) administering by local injection into the joint a therapeutically effective amount of a formulation comprising a pharmaceutically active peptide set forth in SEQ ID NO: 1, and a pharmaceutically acceptable, injectable carrier;
   (iii) obtaining a second image of the subchondral bone using MRI, and measuring 3D bone shape of the subchondral bone from the second MRI image;
   (iv) comparing the 3D bone shape measured from the first MRI image and the second MRI image, and determining responsiveness of the 3D bone shape change to the peptide injection; and
   (v) repeating the injection until the pathological bone shape change in the joint is delayed or reduced, wherein the measuring and comparing of 3D bone shape are performed using active appearance modelling (AAM).

2. The method of claim 1, wherein the repeating of injection is over a period of weeks, and the pharmaceutically active peptide is administered in an amount in a range of 50 to 400 mg±20%.

3. The method of claim 1, wherein the joint is a knee joint.

4. The method of claim 1, wherein the subchondral bone is a femur.

* * * * *

```
                          SEQUENCE LISTING

<160> NUMBER OF SEQ ID NOS: 6

<210> SEQ ID NO 1
<211> LENGTH: 23
<212> TYPE: PRT
<213> ORGANISM: Artificial sequence
<220> FEATURE:
<223> OTHER INFORMATION: synthetic sequence

<400> SEQUENCE: 1

Thr Asp Leu Gln Glu Arg Gly Asp Asn Asp Ile Ser Pro Phe Ser Gly
1               5                   10                  15

Asp Gly Gln Pro Phe Lys Asp
            20

<210> SEQ ID NO 2
<211> LENGTH: 23
<212> TYPE: PRT
<213> ORGANISM: Artificial sequence
<220> FEATURE:
<223> OTHER INFORMATION: synthetic sequence

<400> SEQUENCE: 2

Thr Asp Leu Gln Glu Arg Gly Asp Asn Asp Met Ser Pro Phe Ser Gly
1               5                   10                  15

Asp Gly Gln Pro Phe Lys Asp
            20

<210> SEQ ID NO 3
<211> LENGTH: 23
<212> TYPE: PRT
<213> ORGANISM: Artificial sequence
<220> FEATURE:
<223> OTHER INFORMATION: synthetic sequence

<400> SEQUENCE: 3

Pro Asp Leu Gln Glu Arg Gly Asp Asn Asp Ile Ser Pro Phe Ser Gly
1               5                   10                  15

Asp Gly Gln Pro Phe Lys Asp
            20

<210> SEQ ID NO 4
<211> LENGTH: 23
<212> TYPE: PRT
```

```
<213> ORGANISM: Artificial sequence
<220> FEATURE:
<223> OTHER INFORMATION: synthetic sequence

<400> SEQUENCE: 4

Pro Asp Leu Gln Gly Arg Gly Asp Asn Asp Leu Ser Pro Phe Ser Gly
1               5                   10                  15

Asp Gly Pro Pro Phe Lys Asp
            20

<210> SEQ ID NO 5
<211> LENGTH: 23
<212> TYPE: PRT
<213> ORGANISM: Artificial sequence
<220> FEATURE:
<223> OTHER INFORMATION: synthetic sequence

<400> SEQUENCE: 5

Pro Asp Leu Leu Val Arg Gly Asp Asn Asp Val Pro Pro Phe Ser Gly
1               5                   10                  15

Asp Gly Gln His Phe Met His
            20

<210> SEQ ID NO 6
<211> LENGTH: 20
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid

<400> SEQUENCE: 6

Asp Leu Xaa Xaa Arg Gly Asp Asn Asp Xaa Xaa Pro Phe Ser Gly Asp
1               5                   10                  15

Gly Xaa Xaa Phe
            20
```